United States Patent [19]
Wu et al.

[11] Patent Number: 6,036,650
[45] Date of Patent: Mar. 14, 2000

[54] ULTRASONIC IMAGING SYSTEM AND METHOD WITH RINGDOWN REDUCTION

[75] Inventors: Ching-Chen Wu, Folsom; Gerald L. Litzza, Sacramento; David Bleam, Orangevale; Randall C. Ziegenbein, Sacramento, all of Calif.

[73] Assignee: Endosonics Corporation, Rancho Cordova, Calif.

[21] Appl. No.: 09/153,819

[22] Filed: Sep. 15, 1998

[51] Int. Cl.$^7$ ........................................................ A61B 8/12
[52] U.S. Cl. ............................................ 600/462; 600/447
[58] Field of Search ................................... 600/443, 447, 600/459, 463, 468; 367/138, 99, 69

[56] References Cited

U.S. PATENT DOCUMENTS

| | | |
|---|---|---|
| 4,917,097 | 4/1990 | Proudian et al. . |
| 5,167,233 | 12/1992 | Eberle et al. . |
| 5,183,048 | 2/1993 | Eberle . |
| 5,453,575 | 9/1995 | O'Donnell et al. . |
| 5,601,802 | 2/1997 | Barlow et al. . |
| 5,603,327 | 2/1997 | Eberle et al. . |
| 5,779,644 | 6/1998 | Eberle et al. . |

FOREIGN PATENT DOCUMENTS

| | | |
|---|---|---|
| 2 233 094 B | 2/1994 | United Kingdom . |
| 2 268 806 B | 2/1997 | United Kingdom . |

*Primary Examiner*—Marvin M. Lateef
*Assistant Examiner*—Ali M. Imam
*Attorney, Agent, or Firm*—Flehr Hohbach Test Albritton & Herbert LLP

[57] ABSTRACT

Ultrasonic imaging method and apparatus in which a reference waveform which is substantially free of echoes is modified to be equal to a weighted sum of the reference waveform and filtered signals from the transducing elements which transmit the ultrasonic waves and receive the reflected echoes. The modified waveform is then subtracted from the transducer signals to remove ringdown signals and provide a displayed image which is substantially free of ringdown artifacts.

49 Claims, 14 Drawing Sheets

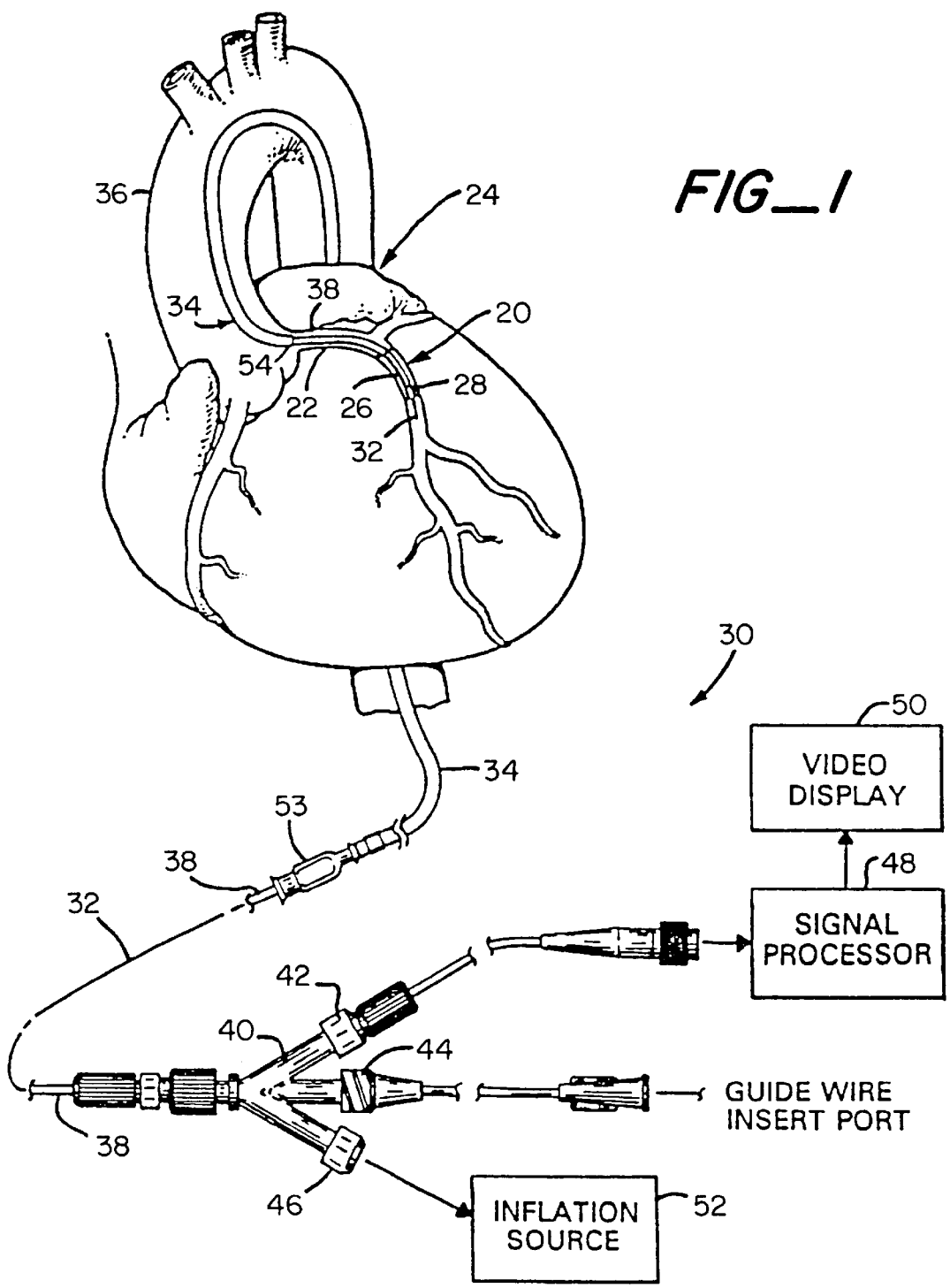
FIG_1

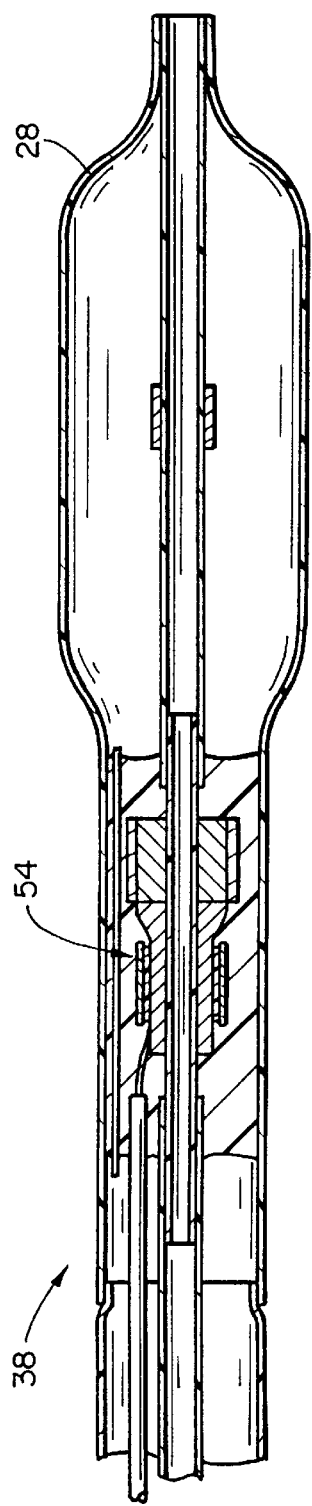
FIG._2A
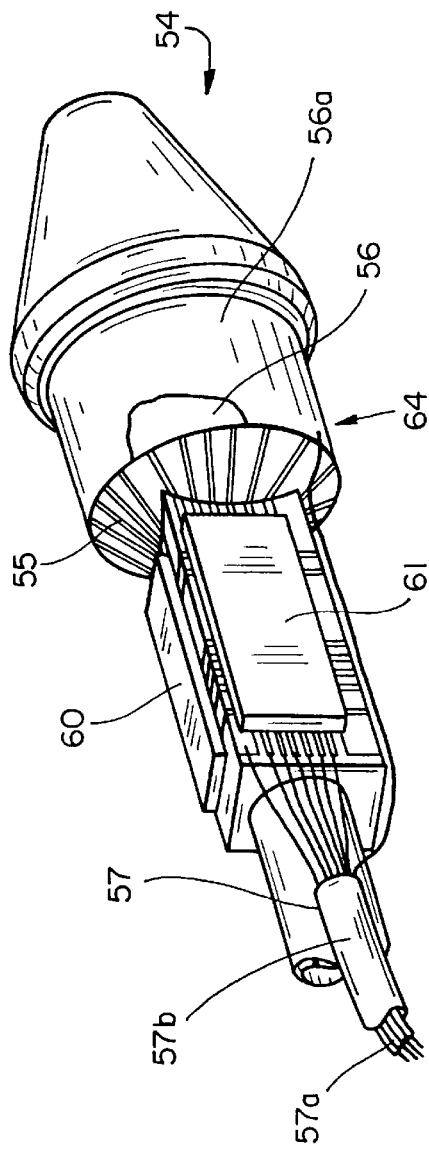
FIG._2B

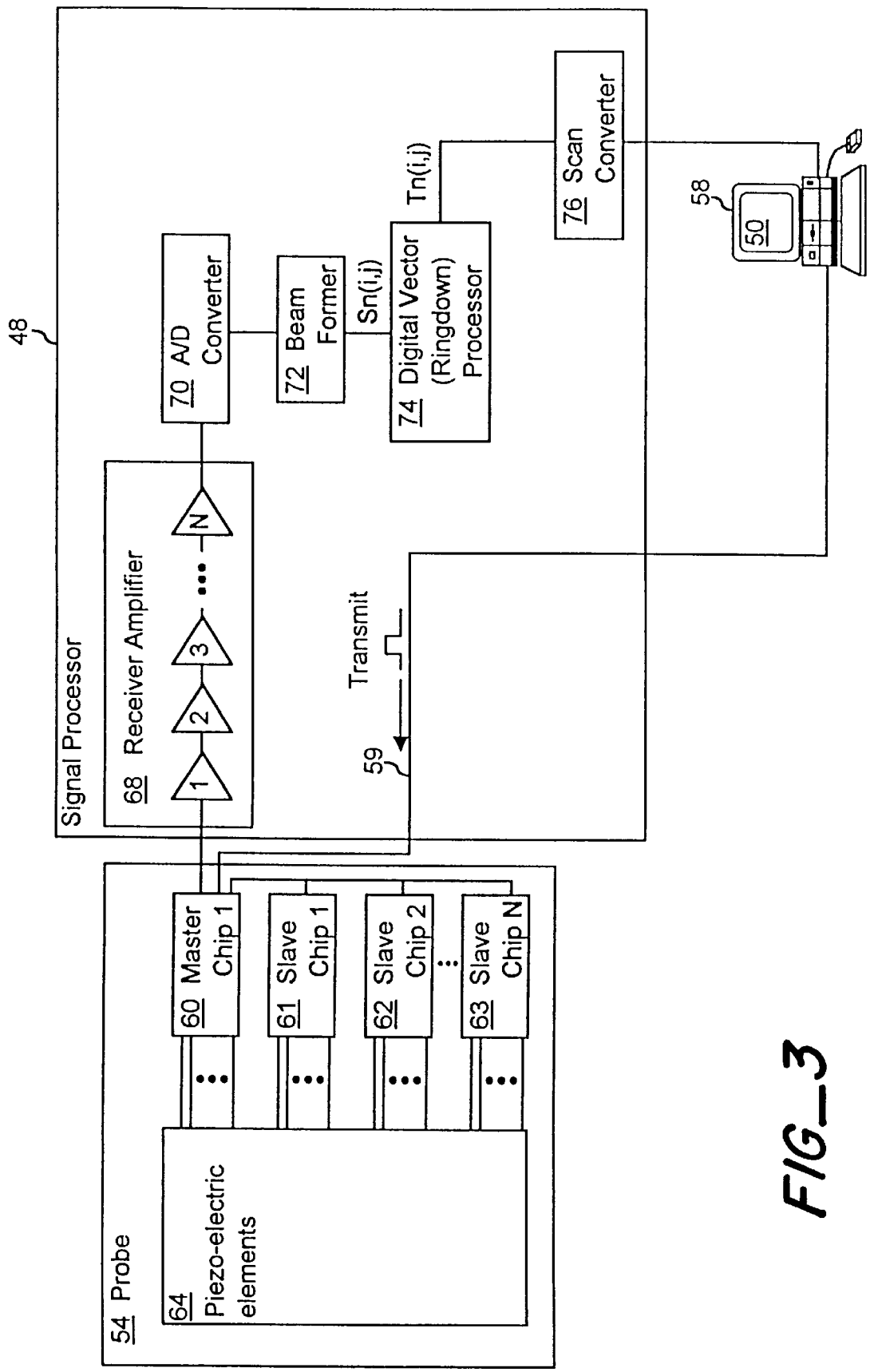
FIG_3

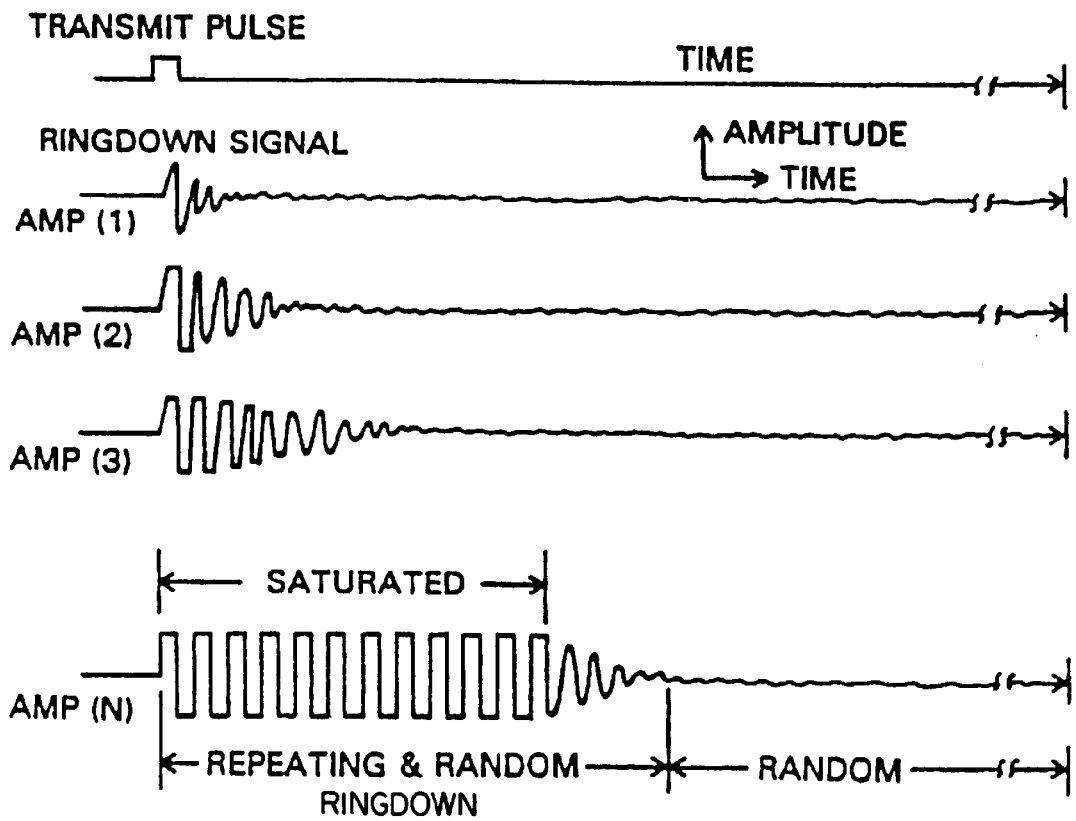
FIG_4
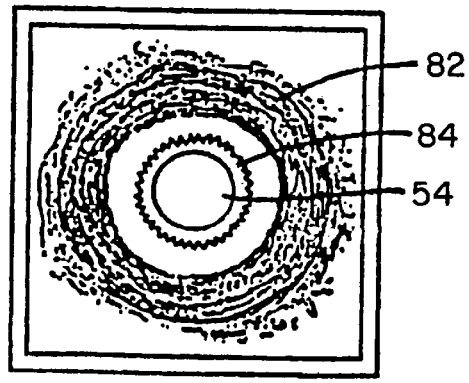
FIG_5

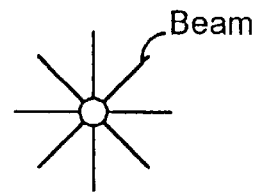
FIG_6A
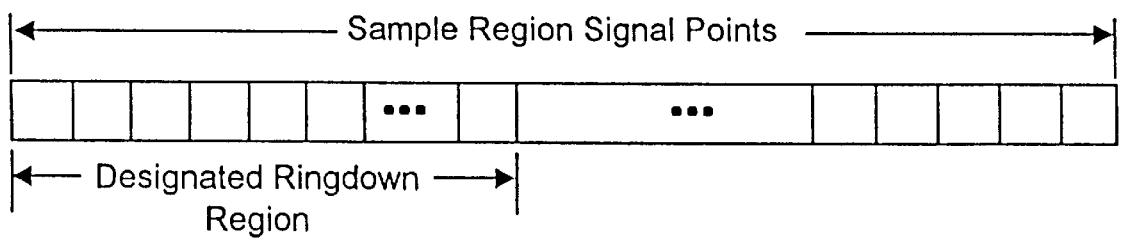
FIG_6B
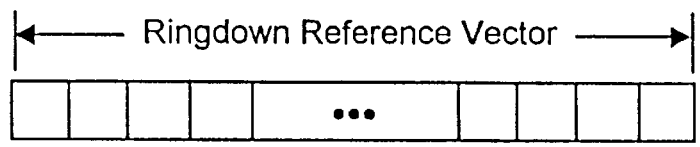
FIG_6C

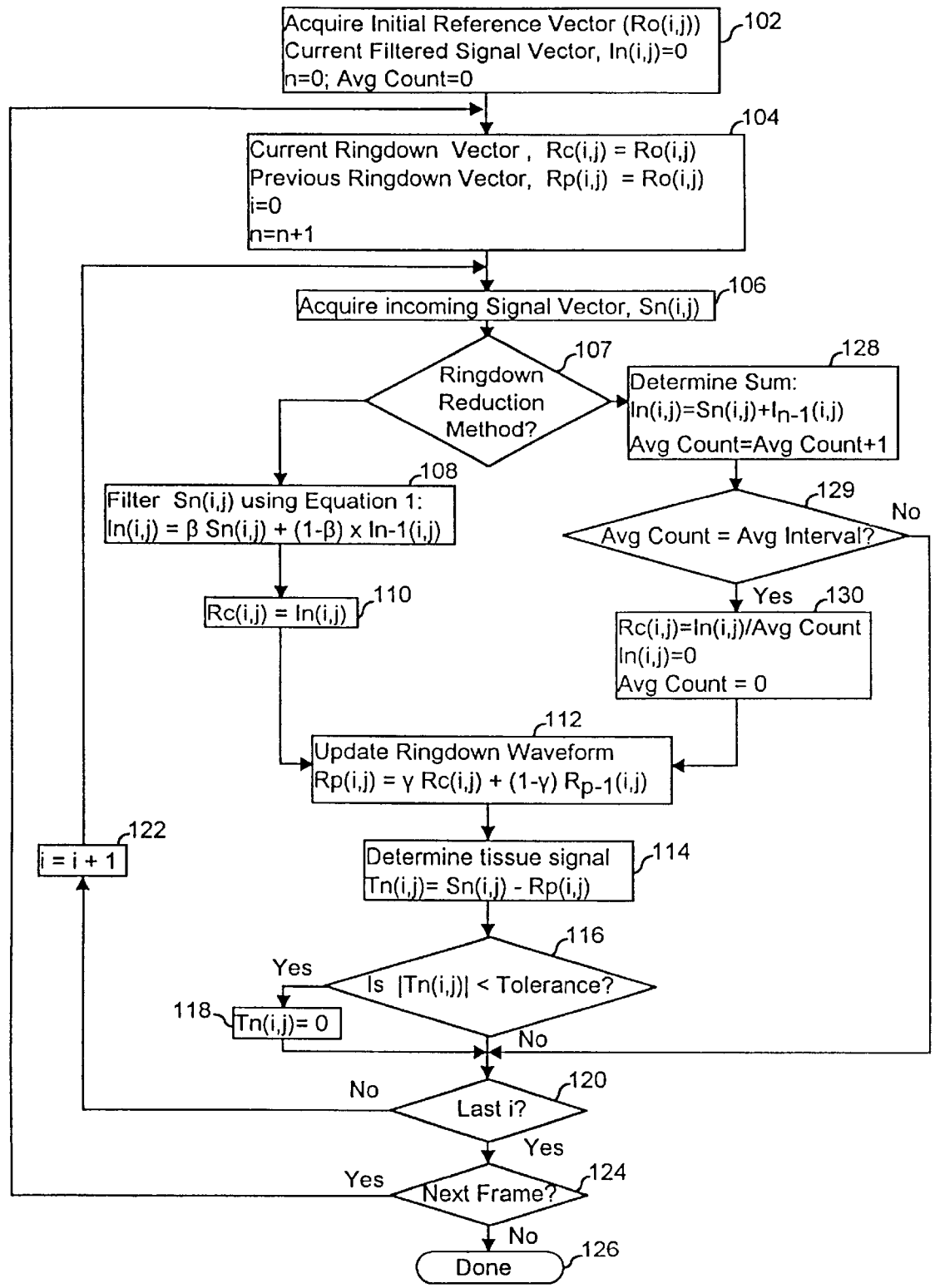
FIG_7

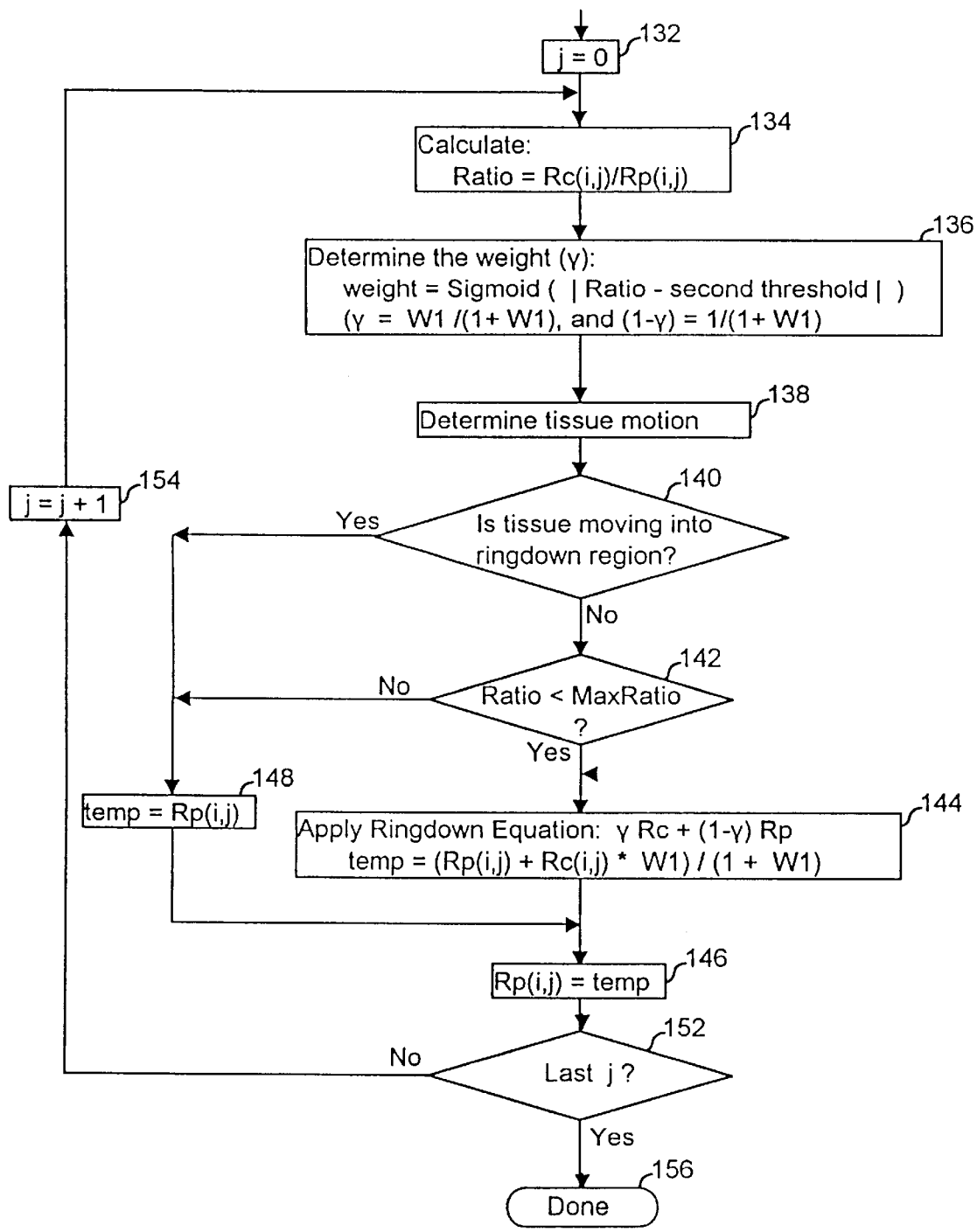
FIG_8A

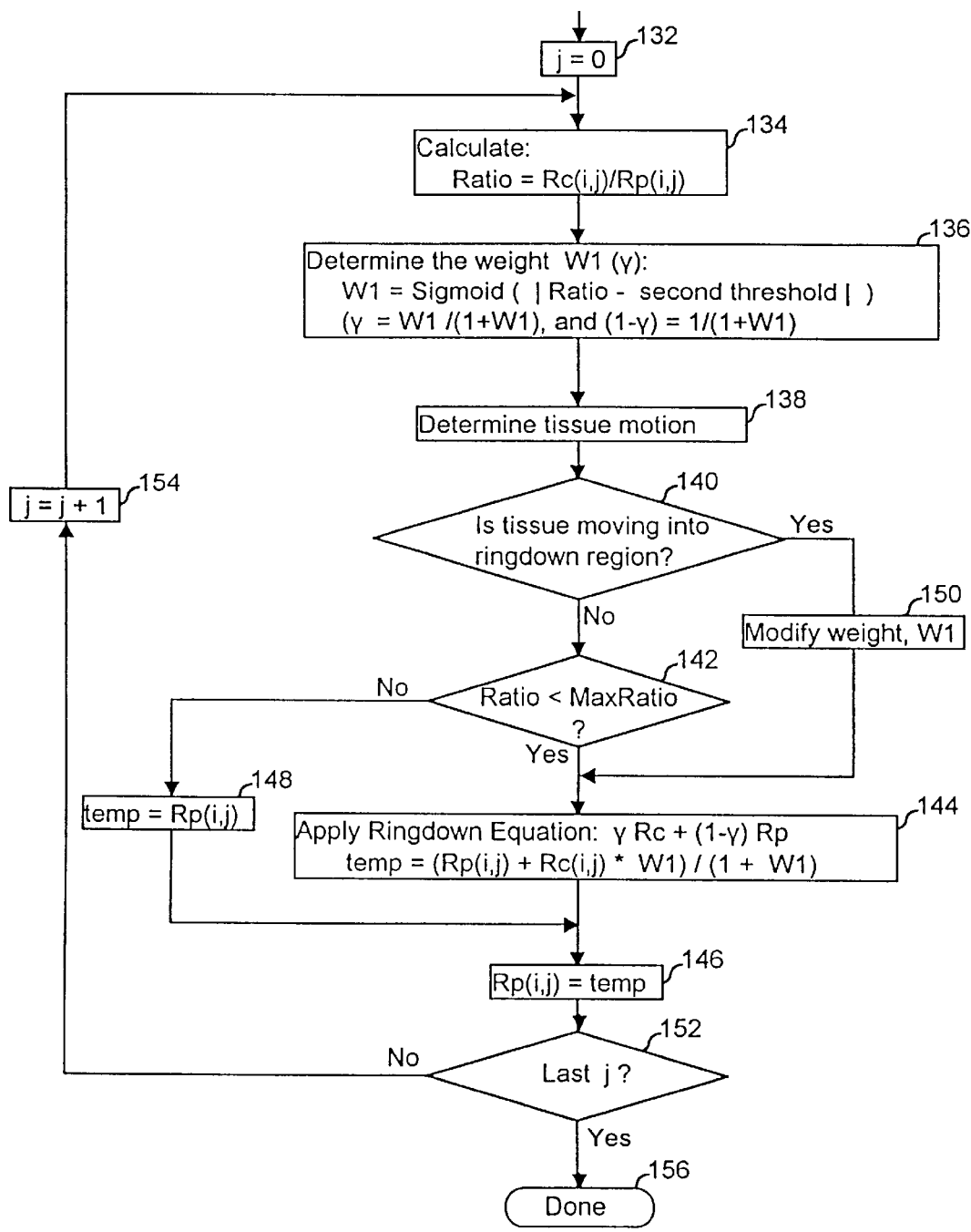
FIG_8B

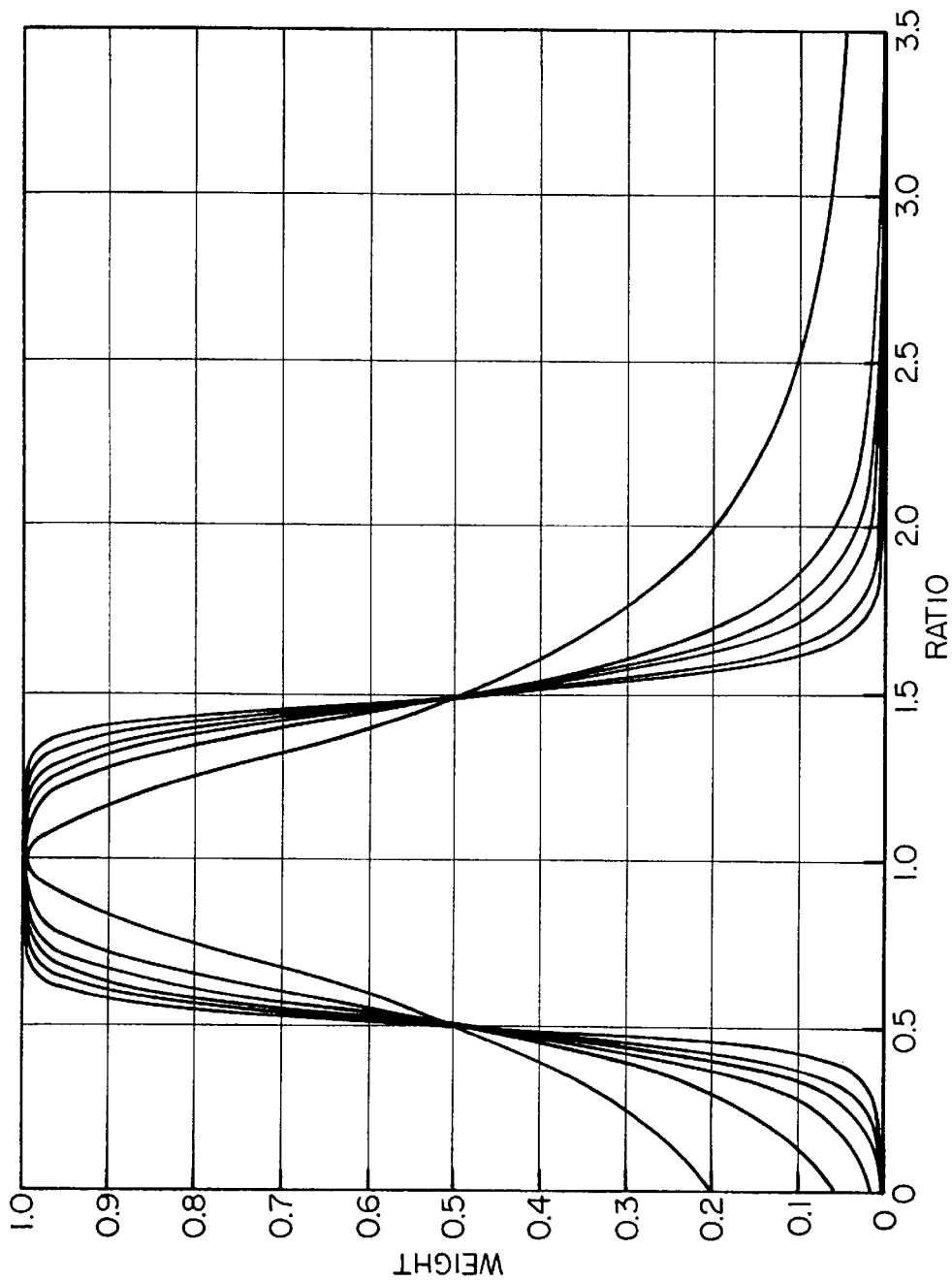
FIG_8C

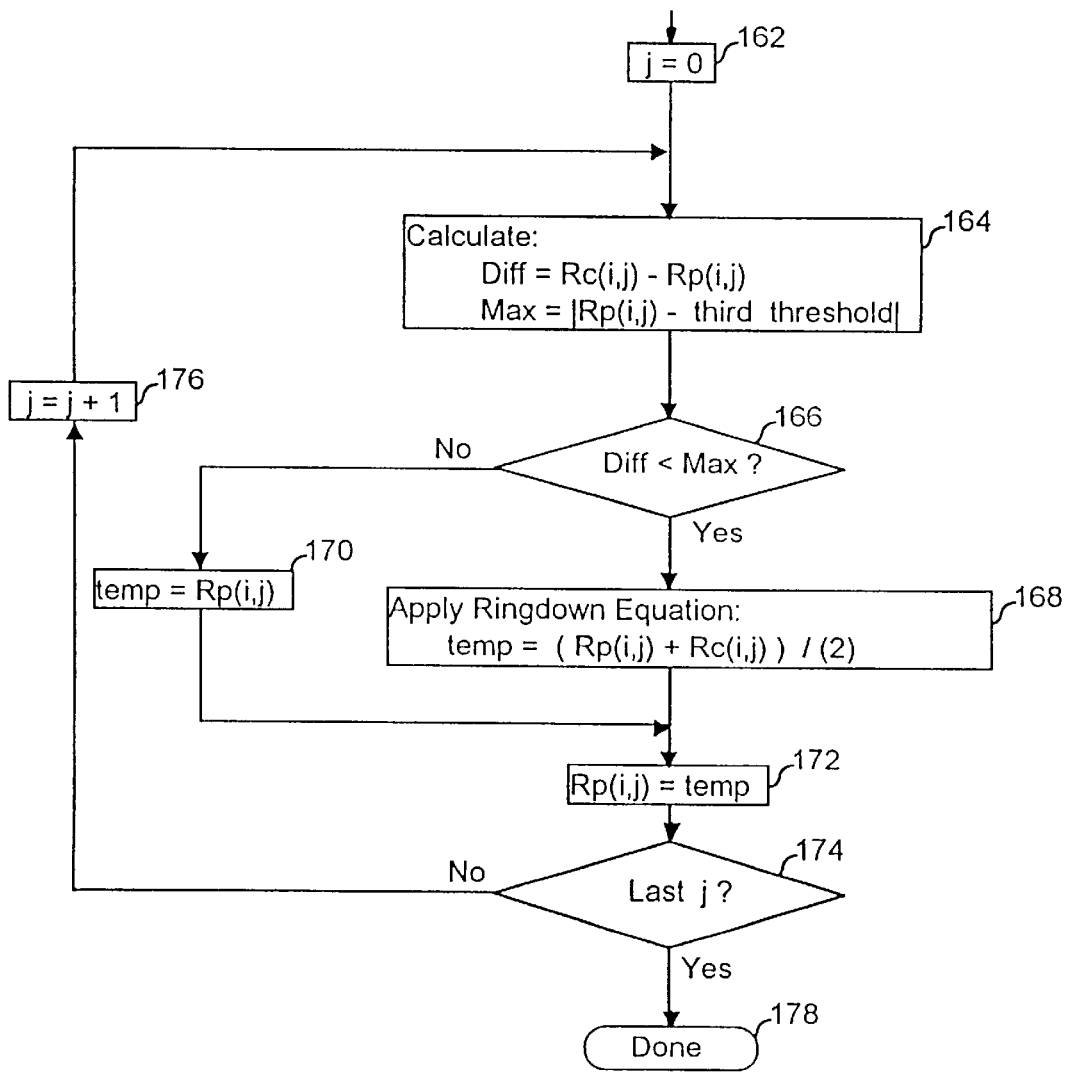
FIG_8D

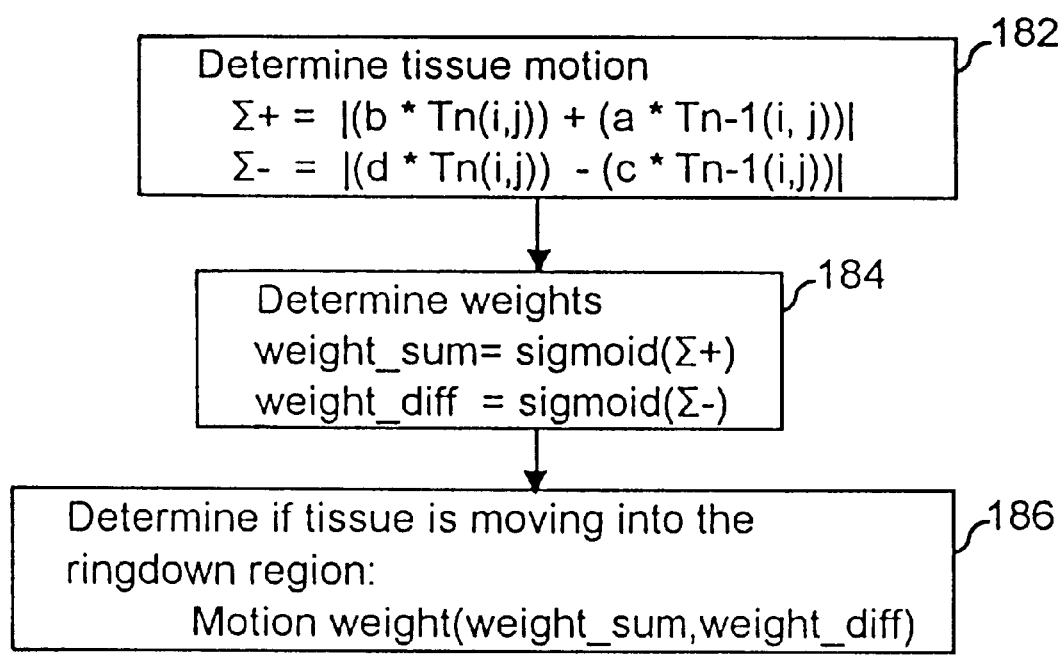
FIG_8E

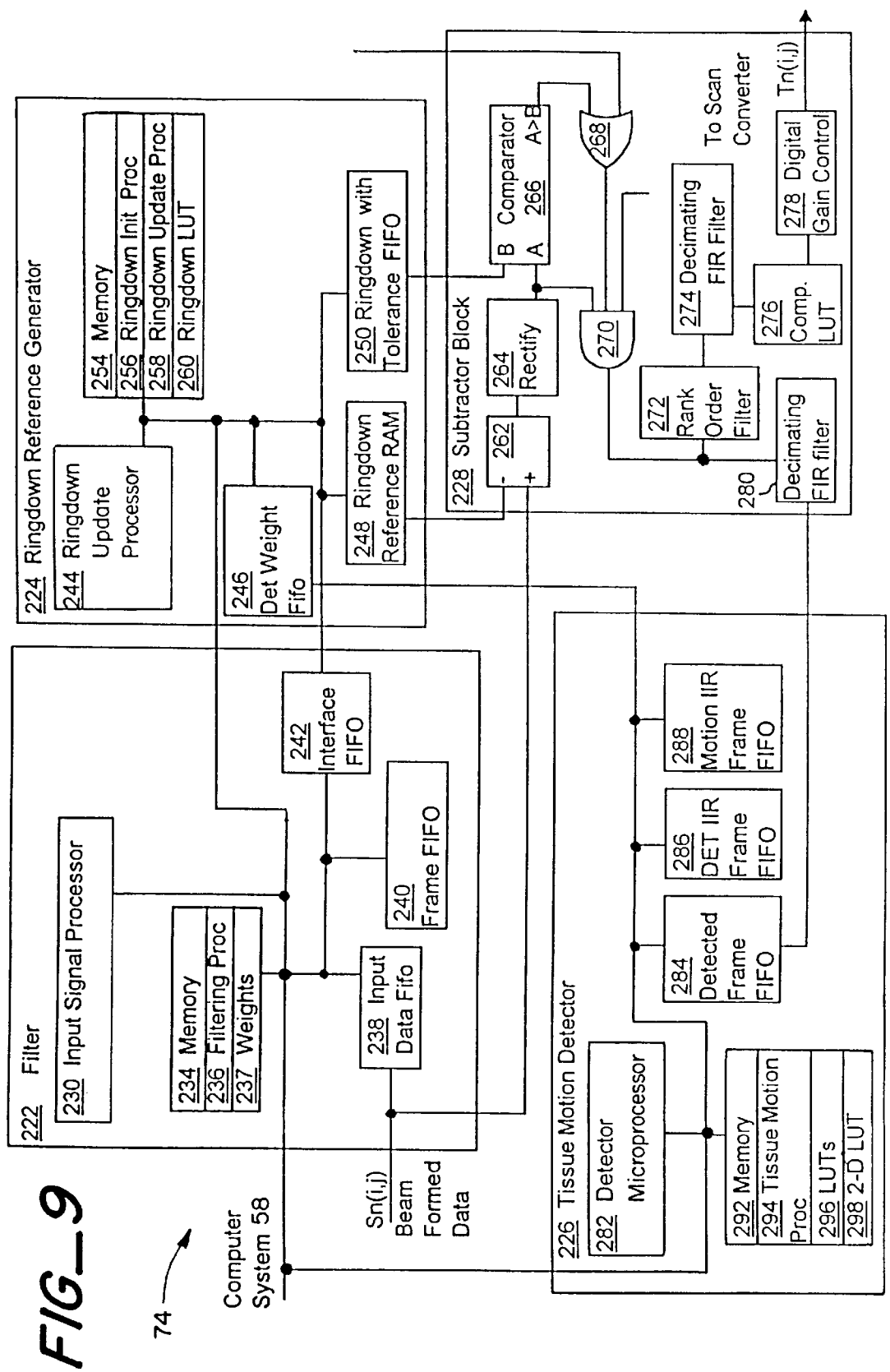
FIG_9

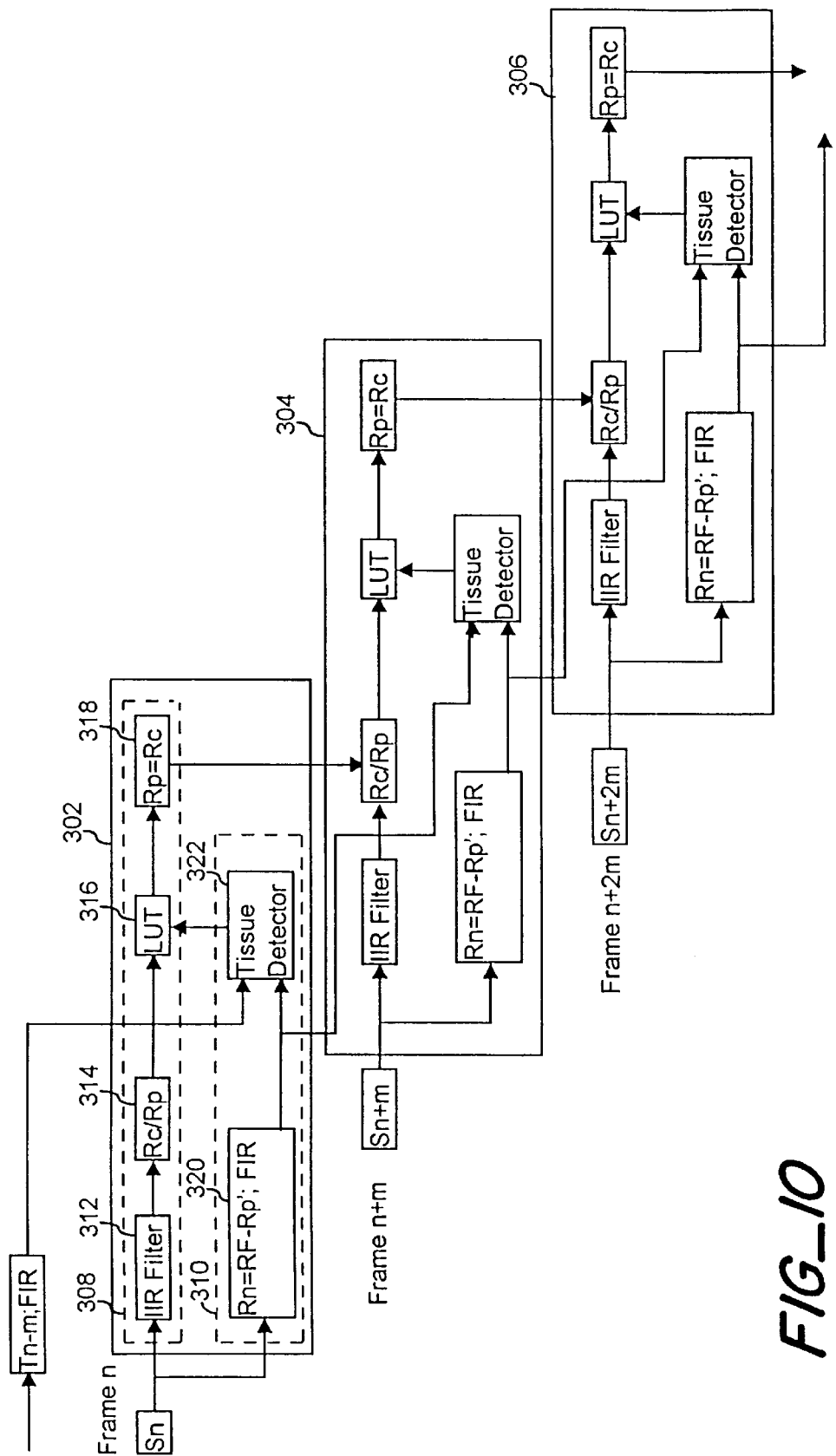
FIG_10

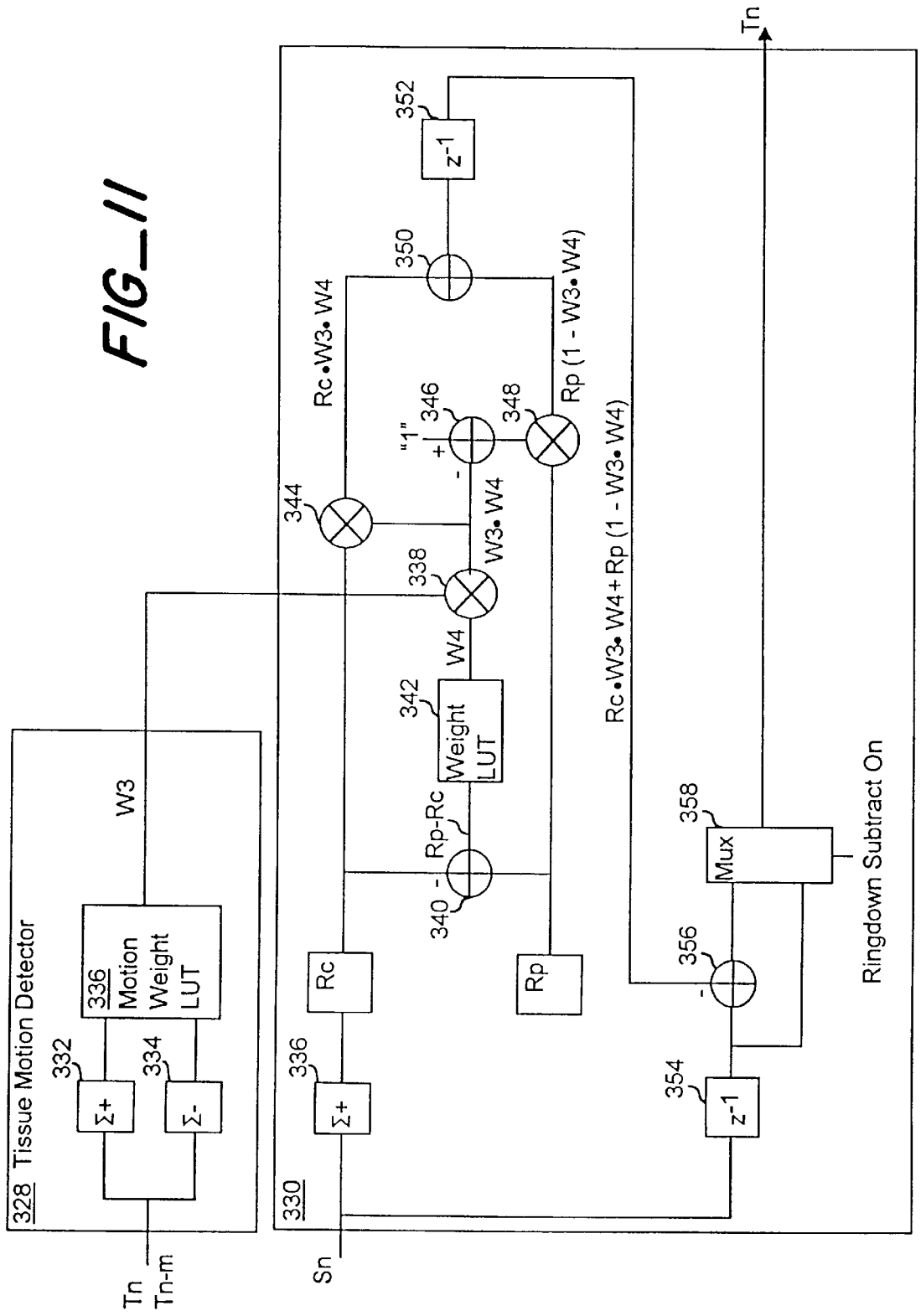

ULTRASONIC IMAGING SYSTEM AND METHOD WITH RINGDOWN REDUCTION

BACKGROUND OF THE INVENTION

1. Field of Invention

This invention relates to ultrasonic imaging and, more particularly, to a method and apparatus for ultrasonically imaging small cavities.

2. Related Art

Ultrasonic imaging devices are used to obtain a visual image of the inner walls and features of a blood vessel for diagnostic purposes. For example, ultrasonic imaging is used to determine the location of a stenotic lesion or stenosis. In addition, ultrasonic transducers are incorporated into interventional devices such as balloon dilation catheters for use in percutaneous transluminal coronary angioplasty (PTCA) to allow imaging and other procedures to be performed with a single instrument.

An ultrasonic image is obtained by inserting a catheter having an ultrasonic transducer at its tip into a blood vessel. Such a transducer typically has a number of piezoelectric elements or other acoustic elements arranged coaxially in a ring around a central guidewire lumen. A computer system individually controls the generation and reception of ultrasonic waves from each element through integrated microcircuits in the catheter tip. The ultrasonic waves reflect off the inner walls and features of the blood vessel, and the transducer elements receive the reflected waves and output an electrical signals in response. The computer system receives the electrical signals from each element, processes the signals, and assembles the processed signals into a digital image for output to a display.

In the displayed image, a visual artifact or blind spot occurs in regions near the elements, and this artifact is commonly referred to as a "ringdown" artifact. The ringdown artifact occurs because the same element both transmits and receives the ultrasonic waves. To generate an ultrasonic wave, an electrical pulse is applied to an element which causes that element to vibrate. After generating the desired ultrasonic wave, the element continues to vibrate or oscillate until the oscillations damp out. This damped oscillation causes the element to generate an electrical signal which is commonly referred to as a "ringdown" signal. The time required for the element to stop vibrating is called the ringdown time. Even during the ringdown time, the element is also being used to "listen" for or sense the echoes from the ultrasonic waves reflecting off tissues.

Initially, the ringdown signal generated by the element is generally a much stronger signal than the signal generated by an echo of the ultrasonic wave. In fact, the ringdown signal can be as much as 80 dB larger than the echo signal.

Because the amplitude of the ringdown signal is so large relative to the echo signal, the ringdown signal saturates the front-end amplifiers of the imaging device circuitry and thus create artifacts in the image. This saturation of the amplifiers effectively creates the blind spot which shows up as a corona in the generated image in an area immediately adjacent the surface of the transducer.

U.S. Pat. No. 5,183,048 to Eberle teaches a method of removing the ringdown signal and reducing artifacts in the displayed image by subtracting a reference waveform corresponding to the ringdown waveform from the imaging data from the elements. The reference waveform is generated or acquired prior to starting the imaging process. It may either be acquired outside the body by placing the catheter in water, or it may be acquired in vivo by placing the catheter in a large vessel to obtain an echo-free waveform.

During normal operation, the ringdown signal drifts in both phase and amplitude over time with respect to the reference waveform, and consequently the reference waveform may not properly compensate for ringdown drift. Many factors affect ringdown drift. One identified source of ringdown drift is temperature change. The temperature of the probe changes during normal operation as the electronics generate heat. Blood flow around the probe also affects the temperature because the blood can act as a coolant. If the blood flow decreases, less heat is removed from the probe and the temperature increases.

The ringdown drift degrades the quality of the image near the tip of the catheter because the reference ringdown waveform no longer reflects the most recent ringdown signal. To compensate for ringdown drift, a new reference ringdown waveform can be generated in a large vessel. However, this method is time consuming and requires repositioning of the catheter.

U.S. Pat. No. 5,601,082 to Barlow et al. teaches a method of removing ringdown drift in which a reference scan is generated and updated it on the basis of a long term running average, then subtracted from a current scan to remove the ringdown. However, that method has also been found to remove the desired tissue echoes or data from the image.

OBJECTS AND SUMMARY OF THE INVENTION

It is, in general, an object of the invention to provide an new and improved method and apparatus for ultrasonically imaging small cavities.

Another object of the invention is to provide a method and apparatus of the above character in which ringdown drift is reduced in the received signal in order to reduce ringdown artifacts in the displayed image.

Another object of the invention is to provide a method and apparatus of the above character which do not require repositioning the catheter in the patient's body to gather a new reference waveform.

These and other objects of the invention are accomplished by providing an ultrasonic imaging method and apparatus in which a reference waveform which is substantially free of echoes is modified to be equal to a weighted sum of the reference waveform and filtered signals from the transducing elements which transmit the ultrasonic waves and receive the reflected echoes. The modified waveform is then subtracted from the transducer signals to remove ringdown signals and provide a displayed image which is substantially free of ringdown artifacts.

BRIEF DESCRIPTION OF THE DRAWINGS

FIG. 1 is a diagrammatic view of one embodiment of an ultrasonic imaging system according to the invention illustrating use of the apparatus to image a coronary artery in connection with a PTCA procedure.

FIG. 2A is an enlarged centerline sectional view of the distal end portion of the dilating balloon catheter in the embodiment of FIG. 1.

FIG. 2B is an enlarged isometric view of the imaging probe inside the dilating balloon catheter in the embodiment of FIG. 2A;

FIG. 3 is a block diagram of one embodiment of an ultrasonic imaging system incorporating the invention.

FIG. 4 is a waveform diagram illustrating operation of the probe in the embodiment of FIG. 2B.

FIG. 5 is an exemplary cross-sectional image of a coronary artery obtained with prior art techniques and ultrasonic imaging apparatus of the type shown in FIG. 1.

FIG. 6A illustrates an exemplary set of beams of a frame produced by the imaging apparatus of FIG. 1.

FIG. 6B illustrates one embodiment of a buffer used for storing a signal vector representing a signal waveform for one of the beams in the embodiment of FIG. 6A.

FIG. 6C illustrates one embodiment of a buffer used for storing a reference vector representing a reference waveform for use in the invention.

FIG. 7 is a flowchart illustrating one embodiment of a method of removing ringdown drift from a signal waveform in accordance with the invention.

FIG. 8A is a flowchart illustrating one embodiment of a method of modifying the reference vector to remove ringdown drift in the embodiment of FIG. 7.

FIG. 8B is a flowchart illustrating another method of modifying the reference vector to remove ringdown drift in the embodiment of FIG. 7.

FIG. 8C is a graphical representation of weighting functions suitable for use in the embodiment of FIG. 8A.

FIG. 8D is a flowchart illustrating another embodiment of a method of updating the reference waveform in the embodiment of FIG. 7.

FIG. 8E is a flowchart illustrating one embodiment of a method of detecting tissue motion in the embodiment of FIG. 7.

FIG. 9 is a functional block diagram of one embodiment of a digital vector processor for use in carrying out the method of FIG. 7.

FIG. 10 is a flow diagram illustrating one embodiment of a method of using the digital vector processor of FIG. 9 for modifying the reference waveform in connection with the detection of tissue motion.

FIG. 11 is a block diagram of another embodiment of a digital vector processor for use in the embodiment of FIG. 7.

DETAILED DESCRIPTION

In FIG. 1, a dilating and imaging apparatus 20 is shown in a coronary artery 22 of a heart 24. This artery contains a buildup of fatty material or plaque 26 which causes the artery to become occluded or stenotic.

Apparatus 20 includes a catheter assembly 30 which has a balloon 28 that is inserted into the artery in a low profile or deflated state, then inflated to treat the stenosis. The catheter assembly 30 includes a guide wire 32, a guide catheter 34 for threading through large arteries such as the aorta 36, and a small diameter catheter 38 that fits inside the guide catheter 34 and is advanced along the guide wire. A tri-arm adapter 40 is provided at the proximal end of the catheter assembly. It has a signal processor port 42 to which a signal processor 48 is connected, a guide wire port 44, and an inflation port 46 to which an inflation source 52 is connected for communication with the interior of the balloon through a fluid lumen in small catheter 38. The small catheter is inserted into the larger guide catheter 34 through a lure lock connector or angioplasty manifold 53. Catheters 34 and 38 can be fabricated be of any suitable flexible material such as polyolefin or polyvinylchloride.

Guide wire 32 is inserted first, followed by guide catheter 34, and then smaller diameter catheter 38 with the dilating balloon 28.

As illustrated in FIG. 2A, a imaging probe 54 is provided in a catheter 38. That probe can provide an image on a visual display 50 associated with signal processor 48, which indicates when the balloon 28 is within a partially blocked area, such as the stenosis 26 of artery 22. After the partially blocked area is located, the catheter 38 is moved to bring the balloon 28 into the blocked area. The balloon 28 is then inflated to expand the stenotic lesion 26 which is causing the blockage. The cardiologist may check the results of the angioplasty procedure. If the procedure was successful, the image on the display 50 will show that the flow passage of the artery 22 has increased in diameter.

As illustrated in FIG. 2B, an array of transducer elements 64 is formed by a plurality of conductive traces 55 on the surface of a cylindrical section of the probe 54 beneath a ring 56 of piezoelectric material. The outer surface of the ring has a thin coating 56a of metallic material which serves as a ground plane for the transducer array. Each element of the array comprises the portion of the piezoelectric material which overlies one of the conductive traces 55. The ring is retained in a fixed position relative to the conductive traces by a film of epoxy glue or other suitable adhesive which bonds the ring to the probe body. The ring is preferably formed as a seamless cylinder of the piezoelectric material, although it may also be formed as a flat sheet which is rolled into a cylinder and joined together at a seam, if desired.

Integrated circuits 60, 61 are mounted on the body of the probe, with conductive traces 55 connecting the integrated circuits to the piezoelectric elements. The conductive traces are evenly spaced about the circumference of the probe 54, with each conductive trace connecting to one transducer element. In one presently preferred embodiment, there are 64 conductive traces and 64 transducer elements.

A cable 57 connects the integrated circuits 60, 61 to the signal processor. The cable comprises a plurality of insulated solid conductors 57a, such as magnet wire, with a copper ribbon surrounding the wires to provide a ground shield, and an insulating jacket 57b surrounding the copper ribbon.

As illustrated in FIG. 3, a computer system 58 delivers excitation pulses to a master chip 60 via a signal processor 48 and a line 59. The master chip 60 cooperates with a number N of slave chips 61, 62, 63 to distribute excitation pulses to the elements in the array of piezoelectric elements 64 on probe 54. Preferably, four slave chips are used. An exemplary probe, transducer array and related circuitry are disclosed in greater detail in U.S. Pat. No. 4,917,097, to Proudian et al., the disclosure of which is incorporated herein by reference. Another exemplary probe, transducer array and related circuitry is disclosed in U.S. Pat. No. 5,779,644, to Eberle et al., which is incorporated herein by reference.

Each element of the array 64 responds to an applied pulse by transmitting an ultrasonic wave into the ambient environment, such as a coronary artery. The chips 60–63 then switch to a receiving mode to detect echoes of the transmitted ultrasonic waves which are produced when transmitted waves are reflected off the inner wall of a blood vessel, or similar small cavity, and impinge upon an element of the array. Upon receiving an echo, the element produces an electrical signal which is detected by the chips 60–63 and transmitted to the signal processor 48.

Signal processor 48 includes a receiving amplifier 68 to which the signals from chips 60–63 are applied, and an analog-to-digital (A/D) converter 70 connected to the output of the receiving amplifier. The output signal from the A/D converter is applied to a beam former 72, and the output of the beam former is applied to a digital vector processor (DVP) 74. The output of the DVP is applied to a scan converter 76 which delivers a signal to the computer for display on video display 50.

The receiving amplifier 68 comprises a series of amplifiers (1), (2), (3) ... (N) for amplifying the low-level signals produced by transducer elements 64. The A/D converter 70 converts the amplified signals to digital form.

Beam former 72 processes the digital signals to generate radial beams of image information as discussed more fully in the aforesaid U.S. Pat. No. 4,917,097, to Proudian et al. The method for the processing of the digital signals to generate radial beams of image formation is also described in U.S. Pat. No. 5,453,575, to O'Donnell et al. which is incorporated herein by reference.

At this point in the signal processing, each beam has an undesired ringdown component in addition to the desired tissue signal or echo. Each beam is represented by a signal vector $S_n(i,j)$, and the tissue signal or echo is represented by a tissue vector $T_n(i,j)$, where n is the frame number, i is the beam number, and j is a signal point within the vector.

The DVP 74 removes the ringdown waveform from the signal vector $S_n(i,j)$ and outputs a tissue waveform as a tissue vector $T_n(i,j)$ to scan converter 76. The scan converter converts the tissue vector $T_n(i,j)$ to a form suitable for viewing on the video display 50 of computer system 58.

FIG. 4 illustrates a series of waveforms showing a ringdown signal being amplified to a point of saturation in the chain of amplifiers (1–N). A transmit pulse excites an element to generate an ultrasonic wave. The element then relaxes according to the characteristic damped oscillation and generates the ringdown signal. The initial high amplitudes of the waveform result from the ringdown signal and are very large in comparison to the amplitudes of the signals generated by reflected echoes. As the waveform is further amplified to an amplitude sufficient for signal processor 48, the ringdown signal is clipped because some of the amplifiers saturate at the high signal amplitudes. For example, the output signal of amplifier (2) begins to saturate in response to the highest amplitudes of the ringdown signal, causing clipping of the waveform. Further amplification of the signal by amplifier (3) causes more of the signal to be clipped. As the ringdown signal continues to be amplified, the output of amplifier (N) has a significant portion of the ringdown signal clipped.

Although large amplification of the waveform causes a significant portion of the ringdown signal to be clipped, this amount of amplification is needed to amplify the much smaller amplitudes of the echo signals to a magnitude which permits the entire waveform to be processed by the signal processor.

In addition, echo signals from tissue near the probe tip are superimposed on the saturated portion of the ringdown signal and may, therefore, be lost because of clipping.

As illustrated in FIG. 5, when the imaging data is processed and displayed, the ringdown signals generate an artifact around the surface of the imaging probe. The image shown in FIG. 5 is an exemplary image showing a vascular cross-section 82, imaging probe 54, and a ringdown artifact 84. The ringdown artifact looks like a corona surrounding the perimeter of the probe. The imaging probe is blind within the corona because any echo information superimposed on the ringdown signal is substantially lost because the ringdown signal saturates the receiving amplifiers.

As shown in FIG. 6A, a frame has many beams or signal vectors, each of which can be represented as $S_n(i,j)$, where $S_n$ is a signal vector for a beam in the $n^{th}$ frame, i is the beam number, and j is a signal point within the signal vector. In the example of FIG. 6B, the signal vector $S_n$ stores signal points, for example, 2,048, for a single beam. The signal vector has a designated ringdown region of signal points, for example, 256, that corresponds to a current ringdown vector. In a preferred embodiment, the number of signal points forming the designated ringdown region is selectable and ranges from zero to 512. The user selects the size of the designated ringdown region by turning a knob while viewing the displayed image. In response to the user, the computer system changes the size of the designated ringdown region in the DVP so that the user can obtain a desirable image. FIG. 6C shows a buffer for storing a reference vector having a predetermined number of signal points, for example, 512 signal points. The reference vector buffer can store less than 512 signal points in response to the user selection of the ringdown region. Because the ringdown signal can vary among elements and therefore among beams, a reference vector is generated for each beam.

In the invention, a modified reference waveform or vector $R_n$ is generated using either of at least two ringdown reduction methods. The appropriate ringdown reduction method for an application is determined and selected during the manufacturing process based on empirical test results.

In a first method of reducing ringdown artifacts of the invention, the modified reference waveform or vector $R_n$ is generated on the basis of a previous reference waveform or vector $R_{n-1}$ and a current signal vector $S_n$ in accordance with the following relationships:

$$I_n = \beta S_n + (1-\beta)I_{n-1} \qquad \text{(Equation 1)}$$

$$R_n = \gamma I_n + (1-\gamma)R_{n-1} \qquad \text{(Equation 2)}$$

In equation (1), $I_n$ is the result of filtering beam $S_n$ to remove noise by performing a weighted sum. Equation (1) is an IIR filter and $\beta$ has a fixed predetermined value between zero and one. During the manufacturing process, $\beta$ is selected based on empirical test results to remove noise for the current application.

Equation (2) is used to generate a modified reference vector $R_n$ which is the result of a weighted sum of $I_n$ and the reference waveform $R_{n-1}$, where $\gamma$ is a weighting factor which is determined as described hereinafter in connection with FIG. 8A. Equation (2) uses the set of signal points of $I_n$ that correspond to the designated ringdown region.

Combining equation (1) with equation (2) results in the following relationship between the modified reference vector $R_n$, the previous reference vector $R_{n-1}$, and the signal vectors $S_n$:

$$R_n = \gamma \beta S_n + \gamma(1-\beta)I_{n-1} + (1-\gamma)R_{n-1} \qquad \text{(Equation 3)}$$

As shown by equation (3), the invention uses two weights, $\gamma$ and $\beta$ and filters the signal vectors $S_n$ before modifying the reference vector $R_n$. In addition, the weight $\gamma$ is chosen based on a relationship between at least one value of a signal point in the ringdown portion of the current signal vector $S_n$ and the reference vector $R_{n-1}$.

In a second method of reducing ringdown artifacts of the present invention, a modified reference waveform or vector $R_n$ is generated on the basis of a previous reference vector $R_{n-1}$ and a current signal vector $S_n$ in accordance with the following relationships:

$$I_n = \left( \sum_{n}^{n+Avg\ Interval} S_n \right) / (Avg\ Interval) \quad \text{(Equation 4)}$$

$$R_n = \gamma I_n + (1-\gamma) R_{n-1} \quad \text{(Equation 2)}$$

In this second method that uses equation (4), $I_n$ is determined in a different manner from that of equation (1), while equation (2) is unchanged. In equation (4), $I_n$ is the result of filtering beams $S_n$ to remove noise by performing a bounded average for at least one group of beams or signal vectors $S_n$. The group has a predetermined number of beams equal to the average interval ("Avg Interval") of equation (4). The reference waveform $R_n$ is modified periodically using equation (2) at the predetermined average interval ("Avg Interval"). In a preferred embodiment, the groups of signal vectors $S_n$ of each bounded average $I_n$ are mutually exclusive.

FIG. 7 is a flowchart illustrating how the reference vector is modified in removing ringdown drift from the signal waveform $S_n$. In step 102, an initial reference vector $R_o$ is acquired by one of the techniques described above, and a frame counter n is set to zero. A current filtered signal vector $I_n(i,j)$ and an average counter (Avg Count) are also initialized to zero. In step 104, current ringdown vector $R_c$ and reference vector $R_p$ are initialized, the signal vector counter i is set to zero, and the frame pointer n is incremented. Vectors $R_c$ and $R_p$ are initialized to $R_o$, and the current averaged or filtered vector $I_n(i,j)$ is set to zero. The designation $R_c$ is shortened notation for $R_n(i,j)$ and $R_p$ is shortened notation for $R_{n-1}(i,j)$.

In step 106, an incoming signal vector $S_n(i,j)$ is acquired. Step 107 determines which ringdown reduction method was selected. If the first method, described above, was selected, in step 108, vector $S_n(i,j)$ is filtered in accordance with equation (1). In step 110, a subset of values in the designated ringdown region of vector $I_n(i,j)$ is deemed to contain the ringdown signal, and designated as $R_c$. Alternatively, the separate designation step can be omitted, and $R_c$ can be represented by a portion of $I_n(i,j)$ that corresponds to the designated ringdown region. In step 112, the reference waveform $R_p$ is updated in accordance with equation (2), as discussed more fully hereinafter in connection with FIG. 8A. In step 114, the updated reference waveform is subtracted from the current echo signal to provide the tissue signal $T_n(i,j)$:

$$T_n(i,j) = S_n(i,j) - R_p(i,j).$$

In step 116, the absolute value of $T_n(i,j)$ is compared with a predetermined tolerance value and if it is within the tolerance limit, then $T_n(i,j)$ is set to zero in step 118, and the process proceeds to step 120. If $T_n(i,j)$ is outside the tolerance, the process proceeds directly to step 120. Step 120 checks to see if all beams $S_n(i,j)$ for a frame have been transformed. If not, step 122 increments i and proceeds to step 106 to process the signal vector for the next beam. If all beams for a frame have been transformed, step 124 determines if the next frame should be processed. If so, step 124 returns to step 104, and the process repeats. If not, the process ends (126).

The tolerance limit in step 116 is the absolute value of the current ringdown vector $R_c$ multiplied by a first threshold value. The first threshold value is a percentage of noise and drift below which the digital vector processor deems that there is no tissue. The first threshold value is determined during the manufacturing process for each probe and varies among probes, and among elements on a probe. In one embodiment, the system reads the tolerance limit from the probe when the probe is plugged in or when power is turned on. In another embodiment, the probe provides a value or a characterization signal to the system which the system uses to determine the first threshold value.

However, if step 107 determines that the second ringdown reduction method was selected, then vector $S_n(i,j)$ will be filtered in accordance with equation (4). In step 128, $I_n$ is used to store a sum of groups of signal vectors such that $I_n(i,j) = S_n(i,j) + I_{n-1}(i,j)$. The average counter (Avg Count) is also incremented. Step 129 determines if the Avg Count is equal to the predetermined average interval (Avg Interval). If not, the method proceeds to step 120. If so, in step 130, the average is determined in accordance with equation (4). In particular, $R_c$ stores the average and is equal to $I_n(i,j)$/Avg Count. In addition, $I_n(i,j)$ and Avg Count are set to zero for the next modification. The ringdown reference waveform is modified in step 112.

The flowchart shown in FIG. 8A illustrates a method of updating the reference vector in step 112 of FIG. 7. In step 132, the signal point index j, which is used to access each signal point of the vector $S_n(i,j)$, is initialized to zero to point to the first signal point of $S_n(i,j)$. In step 134, the ratio of $R_c(i,j)$ to $R_p(i,j)$ is calculated. In step 136, a weight $W_1$ is determined by subtracting a second threshold value from the ratio, and passing the absolute value of the result as a parameter to a ringdown weighting function which returns the weight $W_1$. That weight is then used as follows to determine the values of $\gamma$ and $1-\gamma$ for use in equation (2):

$\gamma = W_1/(1+W_1)$, and $(1-\gamma) = 1/(1+W_1)$.

Like the first threshold value, the second threshold value is based on a characterization signal received from the probe when power is turned on or when a probe is attached to the system.

Alternatively, rather than subtracting a threshold value from the ratio, the ratio itself can be passed as a parameter to the ringdown weighting function.

Step 140, which is discussed in detail in connection with the flowchart of FIG. 8E, determines if tissue is moving into the ringdown region. If tissue is not moving into the ringdown region, step 142 determines if the ratio is less than a predetermined value MaxRatio which is the largest value of the ratio $R_c/R_p$ stored in a look-up table. If the ratio is less than MaxRatio, a modified reference vector signal point, called temp, is determined in step 144 in accordance with the following relationship:

$temp = (R_p(i,j) + R_c(i,j) * W_1)/(1+W_1)$, and then in step 146 temp is stored in $R_p(i,j)$. If the ratio is not less than MaxRatio, then temp is set equal to the current value of $R_p(i,j)$, and that value of temp is once again stored in $R_p(i,j)$ in step 146.

If tissue is determined to be moving into the ringdown region, the routine jumps from step 140 to step 148 and sets temp equal to $R_p(i,j)$, with no modification of the reference waveform.

Step 152 determines if all signal points in the reference vector have been updated. If not, step 154 increments j and returns to step 134. If all signal points have been updated, then the process ends at step 156.

FIG. 8B illustrates an alternate embodiment in which the weight $W_1$ is modified if tissue motion is detected. This embodiment is similar to the embodiment of FIG. 8A except that if tissue movement in the ringdown region is detected in step 140, then the weight $W_1$ is modified in step 150, and the routine proceeds to step 144. Because tissue echoes in the ringdown region may change the amplitude and phase of the signal in the ringdown region, the effect of tissue echoes is scaled or reduced.

FIG. 8C illustrates an exemplary set of sigmoid functions showing the relationship between the weight $W_1$ which is plotted along the y-axis and the ratio $R_c/R_p$ which is plotted along the x-axis. The maximum weight equals 1 when the input parameter equals 1, such as when $|R_c/R_p-\text{second threshold}|$ equals 1 or alternately when $R_c/R_p$ equals 1. The sigmoid function is implemented in a look-up table stored in memory, and the ratio is the index to the look-up table. Since the look-up table stores a finite number of values, MaxRatio is the highest value of $R_c/R_p$ for which the look-up table has a weight. Values of $R_c/R_p$ exceeding MaxRatio are set to a predetermined value such as zero.

A set of weighting functions is shown because ringdown drift varies among elements. In one presently preferred embodiment, when the system is powered on or a probe is attached, the probe sends a weighting function selection signal for all elements of the probe. The system then uses the weighting function selection signal to select the appropriate weighting function that will be used for all the elements. Alternatively, if desired, the probe can send the values of the weighting function for the elements.

For example, if $R_c/R_p$ equals 1, the weight will be equal to 1 because there is no ringdown drift. In this case, $R_p$ and $R_c$ are given equal weight, and the modified reference vector will be equal to $\frac{1}{2}R_c+\frac{1}{2}R_p$.

In contrast, when the ratio $R_c/R_p$ is equal to 0.5, the weight is also equal to 0.5. In this case, the reference vector will be equal to $\frac{2}{3}R_p+\frac{1}{3}R_c$, thereby giving $R_p$ more weight. At most, when the weight is equal to zero, $R_c$ is given half the weight when updating the reference ringdown vector.

FIG. 8D illustrates an alternate method for updating the reference vector, which is called the linear threshold method. This method is similar to the method of FIG. 8A except that the weighting function is a step function in which $R_c$ is given either one-half or no weight. In step 162, j is set to zero, and in step 164 the values Diff and Max are determined:

$$Diff=R_c-R_p$$

$$Max=|R_p*\text{third threshold value}|$$

These values are then compared in step 166. If Diff is less than Max, temp is set equal to the average of $R_p$ and $R_c$ in step 168. If Diff is not less than Max, temp is set equal to $R_p$, the previous value of the ringdown waveform, in step 170. In step 172, $R_p$ is set to temp. Step 174 determines if all signal points were modified. If not, step 176 increments j and returns to step 164. If all signal points were modified, then the routine ends at step 178.

The flowchart of FIG. 8E shows how tissue motion is determined. Typically, over small periods of time, tissue moves, but the ringdown signal is stationary. This means that, over time, the average of $S_n(i,j)$ approaches the ringdown signal $R_n(i,j)$ and the average of $T_n(i,j)$ approaches zero. Therefore, an average can theoretically estimate the stationary ringdown component of the signal. However, if the probe becomes stationary near a vessel wall, the tissue signal will no longer be averaged out, and that can distort the reference waveform. To avoid this problem, the reference waveform is updated with respect to tissue motion.

Both near field and far field tissue motion are determined using the method of FIG. 8E. Near field tissue motion occurs in the region corresponding to the first group of sample points representing the ringdown region. Far field tissue motion occurs in the region corresponding to the next group of sample points, outside the ringdown region. Tissue motion is indicated by a motion weight which, in one embodiment, is computed at every sample point for a given beam. However, the motion weight should not change radically between frames and beams. Therefore, to reduce computation, the motion weight can, if desired, be determined with only a subset of the beams.

Step 182 determines a weighted sum $\Sigma+$ and difference $\Sigma-$ of tissue echoes $T_n(i,j)$ at corresponding sample points in two frames, using the following relationships:

$$\Sigma+=|(b*T_n(i,j))+(a*T_{n-1}(i,j))|, \text{ and}$$

$$\Sigma-=|(d*T_n(i,j))-(c*T_{n-1}(i,j))|.$$

Step 184 determines the weights, weight_sum and weight_diff, for the weighted sum $\Sigma+$ and difference $\Sigma-$, respectively from look-up tables in which the desired weighting functions are stored. Preferably, a sigmoid function similar to that shown in FIG. 8C is stored in the look-up table as the weighting function.

Step 186 passes weight_sum and weight_diff as parameters to a motion function to determine tissue motion and assign a motion weight. The motion function uses the parameters weight_sum and weight_diff to access a two-dimensional motion_weight look-up table that has been stored in memory to determine if tissue has moved.

In a preferred embodiment, the motion weight is assigned a value of zero or one using the motion_weight look-up table in which a zero indicates no motion and a one indicates tissue motion. In the motion_weight lookup table, the distribution of the motion weight values assigned to combinations of weight_sum and weight_diff depends on the values of the weighting coefficients a, b, c and d, the sigmoid function and a predetermined probability that certain values represent tissue motion.

In an alternate embodiment, a range of motion weight values from zero to one are used including fractional motion weights. A fractional motion weight is a fraction representing a probability that tissue is moving. However, for fractional motion weights, the system or system software needs an additional decision function to determine if the fractional motion weight indicates that tissue is moving.

Weight_sum, weight_diff and motion weight look-up tables are determined for each of the signal vectors or beams. As with the other weighting functions, the probe sends a characterization signal which the computer system 58 uses to select and download the desired weighting function to be used by the DVP.

Preferably and ideally, tissue motion is determined for each beam in consecutive frames, and a frame-by-frame sum and difference are calculated for each beam. However, in practice, tissue motion is determined every m frames and the sum and difference are calculated every m frames. In this embodiment, m is a function of the speed of the microprocessor and the size of the designated ringdown region.

A vector processor (DVP) 74 utilizing the techniques of FIGS. 8A–8E is illustrated in FIG. 9. The DVP includes a filter 222, a ringdown reference generator 224, a tissue motion detector 226 and a subtractor block 228.

The filter 222 has an input signal processor 230 and a memory 234. When power is turned on, the system 58 downloads the filtering procedure (Filtering proc) 236 into the memory 234 for execution by the input signal processor 230. For equation (1), the filtering procedure 236 is programmed with a weight (β) 237, and execution of the filtering procedure performs the filtering function of Equation (1) or (4) depending on the selected ringdown reduction method.

An incoming signal vector $S_n(i,j)$ is received in an input data FIFO 238. The input signal processor 230 executes the filtering procedure 236 and filters the input signal vectors stored in the input data FIFO 238. The input signal processor 230 stores the output $I_n(i,j)$ of the filtering procedure 236 in a filter frame FIFO 240 for use in the next filtering operation, and also stores $I_n(i,j)$ in an interface FIFO 242 for output to the ringdown reference generator 224.

The ringdown reference generator 224 includes a ringdown update processor 244, a detected tissue motion weight FIFO 246, a ringdown reference RAM 248 and a ringdown with tolerance FIFO 250 and a memory 254. The computer system 58 downloads a ringdown initialization procedure 256 and a ringdown update procedure 258 for execution by the ringdown update processor 244 into the memory 254 when power is turned on. In addition, the computer system 58 downloads the first threshold value and a ringdown look-up table 260 with the weighting function when power is turned on or when a probe is attached. The ringdown update processor 244 executes the ringdown initialization procedure 256 to provide a reference vector for each beam and stores the reference vectors in the ringdown reference RAM 248. The ringdown initialization procedure 256 also multiplies the first threshold value with the vector stored in the ringdown reference RAM 248 and stores the result in the ringdown with tolerance FIFO 250. The ringdown reference generator 224 executes the function of equation (2) with the filtered vectors $I_n(i,j)$ of the interface FIFO 242 and the reference vectors stored in the ringdown reference RAM 248.

In the subtractor block 228, the input signal vector $S_n(i,j)$ is applied to the positive input of a subtractor 262, and the output of the ringdown reference RAM 248 is applied to the negative input of the subtractor 262 so the subtractor 262 outputs the difference between $S_n(i,j)$ and the corresponding value in the ringdown reference RAM 248. A rectifier 264 provides the absolute value of that difference to the A input of a comparator 266, and the output of the ringdown with tolerance FIFO 250 is applied to the B input of the comparator 266 so that the absolute value is compared with the corresponding vector from the ringdown with tolerance FIFO 250. If the absolute value is greater than the FIFO vector, the comparator 266 outputs a one, which sets OR gate 268 high. That allows the rectified tissue difference to pass through an AND gate 270 for further processing in a rank order filter 272, a decimating FIR filter 274, a compression look-up table 276 and a digital gain control 278 for output to the scan converter.

The rank order filter 272 receives the signals making up the beams from AND gate 270 and places the beams in the proper order for output to the display. Since the beams may not be acquired sequentially, the beams need to be ordered so that adjacent beams will be output sequentially. After processing by decimating FIR filter 274, the signals address the compression look-up table 276, and the compressed signals are passed through a digital gain control 278 to provide an output signal $T_n(i,j)$. A second decimating FIR filter 280 processes the rectified signal passed through AND gate 270 for output to the tissue motion detector 226.

The tissue motion detector 226 has a detector processor 282, a detected frame FIFO 284, a detected infinite impulse response (IIR) frame FIFO 286, a motion IIR frame FIFO 288, and a memory 292. The computer system 58 downloads a tissue motion detection procedure 294 for execution by the detector processor 282 into the memory 292 when power is turned on. The computer system 58 also downloads the sum and difference weighting functions as look-up tables 296, and downloads the two dimensional tissue motion look-up table 298, when power is turned on or when a probe is attached. The computer system 58 loads the coefficients a, b, c and d into the registers of the detector processor 282 to determine the weighted sum and difference. Alternatively, the tissue motion detection procedure 294 can load the values of the coefficients a, b, c, and d into registers of the detector processor 282.

The decimated tissue vector signal from the decimating FIR filter 280 is applied to detector processor 282 which executes the tissue motion detection procedure 294. That procedure 294 implements the method described with respect to FIG. 8E. Detector processor 282 outputs the detected tissue motion weights to the detected weight FIFO 246 of the ringdown reference generator 224, and it uses the DET IIR frame FIFO 286 to store the weighted sum of the tissue motion. It stores the weighted difference in the Motion IIR frame FIFO 288 as described above.

The input signal processor 230, ringdown update processor 244 and detector processor 282 can be microprocessors of any suitable design, and in one presently preferred embodiment they are Texas Instruments TMS320C50 digital signal processors.

The flow diagram of FIG. 10 illustrates how the reference waveform is updated in connection with the detection of tissue motion using the DVP 74. Frames arrive sequentially, and because of timing constraints, DVP 74 updates tissue motion after every m frames for a given beam $S_n(i,j)$, while updating the ringdown reference waveform for every frame. Therefore, the tissue motion update lags the ringdown update by m frames.

FIG. 10 shows a series of three similar updaters 302, 304 and 306, each of which updates both the reference vector and the tissue motion for a beam $S_n$. Each updater has one path 308 for the reference vector and another path 310 for tissue motion.

In the reference vector path, the signal vector $S_n$ is filtered by an IIR filter 312, and the ratio $R_c/R_p$ is determined as indicated at 314. That ratio is then applied to a look-up table 316 to determine a weight function for updating the ringdown reference waveform.

In the tissue motion path, a previous value of the reference waveform $R_p'$ is subtracted from the incoming signal vector $S_n$, and the resulting signal is averaged in a finite impulse response (FIR) filter, as indicated in block 320. The output of the FIR filter is applied to a tissue detector 322 along with a tissue vector from a frame $T_{n-m}(i,j)$ that occurred m frames earlier. The tissue detector 322 determines the weighted sum and difference of $T_{n-m}(i,j)$ and $T_n(i,j)$, applies the appropriate weighting functions to the weighted sum and difference, and applies the two dimensional weighting function described above. The results of tissue motion detection are stored in look-up table 316, and in block 318, those results are used to update the reference waveform, which flows to the next update block.

An alternate embodiment of a tissue motion detector 328 and a ringdown update generator 330 are illustrated in FIG. 11. In tissue motion detector 328, tissue signals $T_n(i,j)$ and $T_{n-m}(i,j)$ for the $i^{th}$ beam of data for frame n and frame n−m are input to an adder 332 and a subtractor 334 which form the weighted sum and difference as described above. The output of the adder 332 and subtractor 334 are applied to look-up tables, including the sigmoid and two-dimensional look-up tables, in the motion weight look-up table 336. The motion weight output W3 of the motion weight look-up table 336 is input to a multiplier 338 in the ringdown update generator 330.

The signal vector $S_n(i,j)$ is input to the ringdown update generator 330 where an adder 336 performs a weighted averaging of the current signal vector $S_n(i,j)$ with a previous weighted average and outputs Rc. Rc and Rp are applied to the inputs of a subtractor 340 which determines the difference between Rp and Rc, and outputs that difference to a look-up table 342. That table implements a weighting function such as shown in FIG. 8C and outputs a weight W4.

Multiplier 338 multiplies weights W3 and W4, and multiplier 344 outputs Rc·W3·W4. Subtractor 346 outputs 1−W3·W4, and multiplier 348 outputs Rp·(1−W3·W4). Adder 350 outputs Rc·W3·W4+Rp·(1−W3·W4) which is equal to Rp+W3·W4(Rc−Rp) and stored in memory 352 for output as Rp.

The signal vector $S_n(i,j)$ is also applied to a memory 354, and the output of this memory is applied to one input of a subtractor 356. The updated ringdown vector Rp from memory 352 is applied to a second input of this subtractor, which thus subtracts the updated ringdown vector Rp from $S_n(i,j)$. Memory 354 acts as a delay line for the signal vector so that the updated ringdown vector will be aligned with it for the subtraction. In other words, the process is delayed so that the reference vector that is subtracted from the signal vector $S_n(i,j)$ is updated with the ringdown signal from the same signal vector $S_n(i,j)$.

The signals from memory 354 and subtractor 356 are applied to the inputs of a multiplexer 358 which outputs the tissue signal $T_n(i,j)$. For signal points in the ringdown region of $S_n(i,j)$, the signal output by the multiplexer will be the signal from the subtractor 356. For signal points outside the ringdown region, it will output the signal $S_n(i,j)$ itself.

Alternatively, rather than determining tissue motion by applying a sum and a difference to the weighting function, a ratio can be applied. Similarly, rather than applying the ratio Rc/Rp to the weighting function, the ringdown reference generator can apply a difference, Rc−Rp, to the weighting function.

The invention has a number of important features and advantages. It provides a method and apparatus for ultrasonically imaging small cavities in which ringdown drift is effectively reduced in the received signal in order to reduce ringdown artifacts in the displayed image, and it does so in a way which does not require repositioning the catheter in the patient's body to gather a new reference waveform.

It is apparent from the foregoing that a new and improved method and apparatus for ultrasonically imaging small cavities have been provided. While only certain presently preferred embodiments have been described in detail, as will be apparent to those familiar with the art, certain changes and modifications can be made without departing from the scope of the invention as defined by the following claims.

What is claimed is:

1. In a method of reducing ringdown artifacts which arise in an ultrasonic imaging system when transducer elements which transmit ultrasonic signals and receive echo signals continue to vibrate after being stimulated to transmit the ultrasonic signals, the steps of:

providing a ringdown reference signal;

modifying the ringdown reference signal to provide a modified reference signal comprising a weighted sum of the ringdown reference signal and filtered transducer signals which contain an echo component and a ringdown component from the transducer elements; and subtracting the modified reference signal from one of the transducer signals to provide an output signal which is substantially free of ringdown artifacts.

2. The method of claim 1 wherein the transducer signals are filtered through an IIR filter.

3. The method of claim 1 wherein the filtered transducer signals include an average of at least one group of transducer signals.

4. The method of claim 3 wherein the at least one group of transducer signals includes a predetermined number of transducer signals.

5. The method of claim 1 further comprising the steps of detecting tissue motion in one of the transducer signals, and modifying the reference signal on the basis of the tissue motion.

6. The method of claim 1 further comprising the step of setting a value of a signal point in the output signal to a predetermined value if the value of the signal point is less than a predetermined tolerance.

7. The method of claim 1 wherein the weighting of the sum is based on relative values of signal points in one of the transducer signals and in the reference signal.

8. The method of claim 1 wherein a ratio of values of signal points in one of the transducer signals and in the reference signal is monitored, and the reference signal is modified if the ratio is less than a predetermined maximum.

9. The method of claim 8 including the steps of applying a predetermined weighting function to the ratio to determine a ringdown weight, and modifying the reference signal on the basis of the ringdown weight.

10. The method of claim 9 wherein the predetermined weighting function is a sigmoid function.

11. The method of claim 9 wherein the ringdown weight is determined from a look-up table.

12. In a method of reducing ringdown artifacts which arise in an ultrasonic imaging system when transducer elements which transmit ultrasonic signals and receive echo signals continue to vibrate after being stimulated to transmit the ultrasonic signals, the steps of:

providing a ringdown reference signal;

modifying the ringdown reference signal to provide a modified reference signal comprising a weighted sum of the ringdown reference signal and filtered transducer signals which contain an echo component and a ringdown component from the transducer elements; and subtracting the modified reference signal from one of the transducer signals to provide an output signal which is substantially free of ringdown artifacts, where $I_n$ represents the filtered transducer signals and is determined in accordance with the relationship:

$$I_n = \beta S_n + (1-\beta)I_{n-1},$$

where $S_n$ is the current transducer signal, $I_{n-1}$ represents previous filtered transducer signals, and $\beta$ is a first weighting factor; and the modified reference signal $R_n$ is determined in accordance with the relationship:

$$R_n = \gamma I_n + (1-\gamma)R_{n-1},$$

where $R_{n-1}$ is a previous reference signal and $\gamma$ is a second weighting factor.

13. In a method of reducing ringdown artifacts which arise in an ultrasonic imaging system when transducer elements which transmit ultrasonic signals and receive echo signals continue to vibrate after being stimulated to transmit the ultrasonic signals, the steps of:

providing a ringdown reference signal;

determining a weighted tissue sum for the current transducer signal and the previous transducer signal;

determining a weighted tissue difference for the current transducer signal and the previous transducer signal;

determining a motion weight based on the weighted tissue sum and the weighted tissue difference;

modifying the ringdown reference signal on the basis of the motion weight to provide a modified reference signal comprising a weighted sum of the ringdown reference signal and filtered transducer signals which contain an echo component and a ringdown component from the transducer elements; and subtracting the modified reference signal from one of the transducer signals to provide an output signal which is substantially free of ringdown artifacts.

14. The method of claim 13 wherein the motion weight is determined by:

applying a first weighting function to the weighted tissue sum to determine a first weight;

applying a second weighting function to the weighted tissue difference to determine a second weight; and applying the first weight and the second weight to a two dimensional tissue motion weighting function to determine a motion weight which indicates whether tissue has moved into a ringdown region.

15. In a method of reducing ringdown artifacts which arise in an ultrasonic imaging system when transducer elements which transmit ultrasonic signals and receive echo signals continue to vibrate after being stimulated to transmit the ultrasonic signals, the steps of:

providing a ringdown reference signal;

modifying the ringdown reference signal to provide a modified reference signal comprising a weighted sum of the ringdown reference signal and filtered transducer signals which contain an echo component and a ringdown component from the transducer elements; and subtracting the modified reference signal from one of the transducer signals to provide an output signal which is substantially free of ringdown artifacts, where $I_n$ represents the filtered transducer signals and is determined in accordance with the relationship:

$$I_n = \beta S_n + (1-\beta) I_{n-1},$$

where $S_n$ is the current transducer signal, $I_{n-1}$ represents previous filtered transducer signals, and $\beta$ is a first weighting factor; and the modified reference signal $R_n$ is determined in accordance with the relationship:

$$R_n = (I_n + R_{n-1} \cdot W1)/(1+W1)$$

where $R_{n-1}$ is a previous reference signal and W1 is another weighting factor.

16. The method of claim 15 wherein a ratio of values of signal points in one of the transducer signals and in the reference signal is monitored, and the reference signal is modified if the ratio is less than a predetermined maximum.

17. In a method of reducing ringdown artifacts which arise in an ultrasonic imaging system when transducer elements which transmit ultrasonic signals and receive echo signals continue to vibrate after being stimulated to transmit the ultrasonic signals, the steps of:

providing a ringdown reference signal;

modifying the ringdown reference signal to provide a modified reference signal comprising a weighted sum of the ringdown reference signal and filtered transducer signals which contain an echo component and a ringdown component from the transducer elements; and subtracting the modified reference signal from one of the transducer signals to provide an output signal which is substantially free of ringdown artifacts, where $I_n$ represents the filtered transducer signals and is determined in accordance with the relationship:

$$I_n = \beta S_n + (1-\beta) I_{n-1},$$

where $S_n$ is the current transducer signal, $I_{n-1}$ represents previous filtered transducer signals, and $\beta$ is a first weighting factor; and the modified reference signal $R_n$ is determined in accordance with the relationship:

$$R_n = (I_n + R_{n-1})/2$$

where $R_{n-1}$ is a previous reference signal.

18. In a method of reducing ringdown artifacts which arise in an ultrasonic imaging system when transducer elements which transmit ultrasonic signals and receive echo signals continue to vibrate after being stimulated to transmit the ultrasonic signals, the steps of:

providing a ringdown reference signal;

modifying the ringdown reference signal to provide a modified reference signal comprising a weighted sum of the ringdown reference signal and filtered transducer signals which contain an echo component and a ringdown component from the transducer elements; and subtracting the modified reference signal from one of the transducer signals to provide an output signal which is substantially free of ringdown artifacts, where $I_n$ represents the filtered transducer signals and is determined in accordance with the relationship:

$$I_n = S_n + I_{n-1},$$

where $S_n$ is the current transducer signal, $I_{n-1}$ represents previous filtered transducer signals and is a sum of n-1 previous transducer signals; and the modified reference signal $R_n$ is determined in accordance with the relationship:

$$R_n = I_n/n,$$

where n is the number of transducer signals included in the sum $I_n$.

19. The method of claim 18 wherein $R_n$ is determined after n transducer signals are summed.

20. In a system for reducing ringdown artifacts which arise in ultrasonic imaging when transducer elements which transmit ultrasonic signals and receive echo signals continue to vibrate after being stimulated to transmit the ultrasonic signals:

means for providing a ringdown reference signal;

means for modifying the ringdown reference signal to provide a modified reference signal comprising a weighted sum of the ringdown reference signal and filtered transducer signals which contain an echo component and a ringdown component; and means subtracting the modified reference signal from one of the transducer signals to provide an output signal which is substantially free of ringdown artifacts.

21. The system of claim 20 wherein the means for modifying the ringdown reference signal includes an IIR filter for filtering the transducer signals.

22. The system of claim 20 wherein the means for modifying the ringdown reference signal includes means for averaging at least one group of transducer signals.

23. The system of claim 22 wherein the at least one group of transducer signals includes a predetermined number of transducer signals.

24. The system of claim 20 further including a tissue motion detector for monitoring the transducer signals and providing a weighting factor corresponding to tissue motion for use by the means for modifying the ringdown reference signal to provide the modified reference signal.

25. In a system for reducing ringdown artifacts which arise in ultrasonic imaging when transducer elements which transmit ultrasonic signals and receive echo signals continue to vibrate after being stimulated to transmit the ultrasonic signals:

means for providing a ringdown reference signal;
means for modifying the ringdown reference signal to provide a modified reference signal comprising a weighted sum of the ringdown reference signal and filtered transducer signals which contain an echo component and a ringdown component; and
means subtracting the modified reference signal from one of the transducer signals to provide an output signal which is substantially free of ringdown artifacts,
where $I_n$ represents the filtered transducer signals and the means for modifying determines $I_n$ in accordance with the relationship:

$$I_n = \beta S_n + (1-\beta) I_{n-1},$$

where $S_n$ is the current transducer signal, $I_{n-1}$ represents previous filtered transducer signals, and $\beta$ is a first weighting factor; and
modifies the ringdown reference signal $R_n$ in accordance with the relationship:

$$R_n = \gamma I_n + (1-\gamma) R_{n-1},$$

where $R_{n-1}$ is a previous reference signal and $\gamma$ is a second weighting factor.

26. In a system for reducing ringdown artifacts which arise in ultrasonic imaging when transducer elements which transmit ultrasonic signals and receive echo signals continue to vibrate after being stimulated to transmit the ultrasonic signals:

means for providing a ringdown reference signal;
means for modifying the ringdown reference signal to provide a modified reference signal comprising a weighted sum of the ringdown reference signal and filtered transducer signals which contain an echo component and a ringdown component; and
means subtracting the modified reference signal from one of the transducer signals to provide an output signal which is substantially free of ringdown artifacts,
where $I_n$ represents the filtered transducer signals and the means for modifying determines $I_n$ in accordance with the relationship:

$$I_n = \beta S_n + (1-\beta) I_{n-1},$$

where $S_n$ is the current transducer signal, $I_{n-1}$ represents previous filtered transducer signals, and $\beta$ is a first weighting factor, and
modifies the ringdown reference signal $R_n$ in accordance with the relationship:

$$R_n = (I_n + R_{n-1} \cdot W1)/(1+W1)$$

where $R_{n-1}$ is a previous reference signal and $W1$ is another weighting factor.

27. The system of claim 26 wherein a ratio of value of signal points in one of the transducer signals and in the reference signal is monitored, and the reference signal is modified if the ratio is less than a predetermined maximum.

28. In a system for reducing ringdown artifacts which arise in ultrasonic imaging when transducer elements which transmit ultrasonic signals and receive echo signals continue to vibrate after being stimulated to transmit the ultrasonic signals:

means for providing a ringdown reference signal;
means for modifying the ringdown reference signal to provide a modified reference signal comprising a weighted sum of the ringdown reference signal and filtered transducer signals which contain an echo component and a ringdown component; and
means subtracting the modified reference signal from one of the transducer signals to provide an output signal which is substantially free of ringdown artifacts,
where $I_n$ represents the filtered transducer signals and the means for modifying determines $I_n$ in accordance with the relationship:

$$I_n = \beta S_n + (1-\beta) I_{n-1},$$

where $S_n$ is the current transducer signal, $I_{n-1}$ represents previous filtered transducer signals, and $\beta$ is a first weighting factor; and
modifies the ringdown reference signal $R_n$ in accordance with the relationship:

$$R_n = (I_n + R_{n-1})/2$$

where $R_{n-1}$ is a previous ringdown reference signal.

29. In a system for reducing ringdown artifacts which arise in ultrasonic imaging when transducer elements which transmit ultrasonic signals and receive echo signals continue to vibrate after being stimulated to transmit the ultrasonic signals:

means for providing a ringdown reference signal;
means for modifying the ringdown reference signal to provide a modified reference signal comprising a weighted sum of the ringdown reference signal and filtered transducer signals which contain an echo component and a ringdown component; and
means subtracting the modified reference signal from one of the transducer signals to provide an output signal which is substantially free of ringdown artifacts,
where $I_n$ represents the filtered transducer signals and the means for modifying determines $I_n$ in accordance with the relationship:

$$I_n = S_n + I_{n-1},$$

where $S_n$ is the current transducer signal, $I_{n-1}$ represents previous filtered transducer signals and is a sum of n−1 previous transducer signals; and
modifies the ringdown reference signal $R_n$ in accordance with the relationship:

$$R_n = I_n/n,$$

where n is the number of transducer signals included in the sum $I_n$.

30. The system of claim 29 wherein $R_n$ is determined after n transducer signals are summed.

31. In a method of reducing ringdown artifacts which arise in an ultrasonic imaging system when transducer elements which transmit ultrasonic signals and receive echo signals continue to vibrate after being stimulated to transmit the ultrasonic signals, the steps of:

providing a ringdown reference signal;

detecting tissue motion in one of the transducer signals from the transducer elements which contains an echo component and a ringdown component;

modifying the ringdown reference signal to provide a modified reference signal based on the detected tissue motion; and subtracting the modified reference signal from one of the signals from the transducer elements to provide an output signal which is substantially free of ringdown artifacts.

32. In a method of reducing ringdown artifacts which arise in an ultrasonic imaging system when transducer elements which transmit ultrasonic signals and receive echo signals continue to vibrate after being stimulated to transmit the ultrasonic signals, the steps of:

providing a ringdown reference signal;

detecting tissue motion in one of the transducer signals from the transducer elements which contains an echo component and a ringdown component;

modifying the ringdown reference signal to provide a modified reference signal based on the detected tissue motion; and subtracting the modified reference signal from one of the signals from the transducer elements to provide an output signal which is substantially free of ringdown artifacts;

wherein the tissue motion is detected and the reference signal is modified by:

determining a weighted tissue sum for a current transducer signal and a previous transducer signal;

determining a weighted tissue difference for the current transducer signal and the previous transducer signal;

determining a motion weight based on the weighted tissue sum and the weighted tissue difference; and modifying the reference signal on the basis of the motion weight.

33. The method of claim 32 wherein $T_n(i,j)$ is a current echo, $T_{n-m}(i,j)$ is a previous echo, the weighted tissue sum is equal to $|(b*T_n(i,j))+(a*T_{n-m}(i,j))|$, and the weighted tissue difference is equal to $|(d*T_n(i,j))-(c*T_{n-m}(i,j))|$.

34. In a system for reducing ringdown artifacts which arise in an ultrasonic imaging system when transducer elements which transmit ultrasonic signals and receive echo signals continue to vibrate after being stimulated to transmit the ultrasonic signals:

means for providing a ringdown reference signal;

means for detecting tissue motion in one of the transducer signals from the transducer elements which contains an echo component and a ringdown component;

means for modifying the ringdown reference signal to provide a modified reference signal based on the detected tissue motion; and means for subtracting the modified reference signal from one of the signals from the transducer elements to provide an output signal which is substantially free of ringdown artifacts.

35. In a system for reducing ringdown artifacts which arise in an ultrasonic imaging system when transducer elements which transmit ultrasonic signals and receive echo signals continue to vibrate after being stimulated to transmit the ultrasonic signals:

means for providing a ringdown reference signal;

means responsive to signals from the transducer elements for detecting tissue motion which contains an echo component and a ringdown component by generating a weighted tissue sum from a weighted sum of a current transducer signal and a previous transducer signal, generating a weighted tissue difference from a weighted difference of the current transducer signal and the previous transducer signal, and determining a motion weight based on the weighted tissue sum and the weighted tissue difference;

means for modifying the ringdown reference signal on the basis of the motion weight to provide a modified reference signal based on the detected tissue motion; and means for subtracting the modified reference signal from one of the signals from the transducer elements to provide an output signal which is substantially free of ringdown artifacts.

36. The system of claim 35 wherein $T_n(i,j)$ is a current echo, $T_{n-m}(i,j)$ is a previous echo, the weighted tissue sum is equal to $|(b*T_n(i,j))+(a*T_{n-m}(i,j))|$, and the weighted tissue difference is equal to $|(d*T_n(i,j))-(c*T_{n-m}(i,j))|$.

37. In a method of reducing ringdown artifacts which arise in an ultrasonic imaging system when transducer elements which transmit ultrasonic signals and receive echo signals continue to vibrate after being stimulated to transmit the ultrasonic signals, the steps of:

providing a ringdown reference signal;

selecting one weighting factor of a plurality of weighting factors based on a characterization signal for one of the transducer elements;

modifying the reference signal by applying the weighting factor to transducer signals and to the reference signal; and subtracting the modified reference signal from one of the transducer signals to provide an output signal which is substantially free of ringdown artifacts.

38. In a method of reducing ringdown artifacts which arise in an ultrasonic imaging system when transducer elements which transmit ultrasonic signals and receive echo signals continue to vibrate after being stimulated to transmit the ultrasonic signals, the steps of:

providing a ringdown reference signal;

selecting one weighting factor of a plurality of weighting factors based on a characterization signal for one of the transducer elements;

modifying the reference signal by applying the weighting factor to transducer signals and to the reference signal; and subtracting the modified reference signal from one of the transducer signals to provide an output signal which is substantially free of ringdown artifacts;

wherein the tissue motion is detected and the reference signal is modified by:

generating a weighted tissue sum from a weighted sum of a current transducer signal and a previous transducer signal;

generating a weighted tissue difference from a weighted difference of the current transducer signal and the previous transducer signal;

determining a motion weight based on the weighted tissue sum and the weighted tissue difference; and modifying the reference signal on the basis of the motion weight.

39. The method of claim 38 wherein the reference signal is modified to be equal to a weighted sum of the reference signal and transducer signals based on the weighting factor.

40. The method of claim 38 further comprising the steps of detecting tissue motion in one of the transducer signals, and modifying the reference signal on the basis of the tissue motion.

41. An ultrasonic imaging system comprising:

a probe assembly having a plurality of elements for transmitting ultrasonic signals and receiving echo signals in response thereto;

at least one amplifier for amplifying signals from the elements, the signals having a ringdown component arising from continued vibration of the elements after the ultrasonic signals are transmitted and a tissue component corresponding to the echo signals;

an analog-to-digital converter for converting the amplified signals to digital signals;

a beam former for transforming the digital signals from a plurality of elements into beams having both a ringdown component and a tissue component;

a filter for reducing noise in the beams;

a ringdown reference generator for generating a ringdown reference signal, and modifying the reference signal to provide a modified reference signal comprising a weighted sum of the reference signal and the filtered beams;

a subtractor for subtracting the modified reference signal from one of the beams to provide an output signal which is substantially free of ringdown artifacts;

a scan converter for converting the output signal to a display signal; and a display responsive to the display signal for providing a visual image.

42. The ultrasonic imaging system of claim 41 wherein the filter averages at least one group of the beams, and the ringdown reference generator modifies the reference signal to be equal to a weighted sum of the reference signal and the average of the at least one group of the beams.

43. The ultrasonic imaging system of claim 41 further including a tissue motion detector for detecting tissue motion in a ringdown region of the beams, and the ringdown reference generator is responsive to a signal from the tissue motion detector in modifying the reference signal.

44. The ultrasonic imaging system of claim 41 wherein a ratio of values of signal points in one of the transducer signals and in the reference signal is monitored, and the reference signal is modified if the ratio is less than a predetermined maximum.

45. An ultrasonic imaging system comprising:

a probe assembly having a plurality of elements for transmitting ultrasonic signals and receiving echo signals in response thereto;

at least one amplifier for amplifying signals from the elements, the signals having a ringdown component arising from continued vibration of the elements after the ultrasonic signals are transmitted and a tissue component corresponding to the echo signals;

an analog-to-digital converter for converting the amplified signals to digital signals;

a beam former for transforming the digital signals from a plurality of elements into beams having both a ringdown component and a tissue component;

a filter for reducing noise in the beams;

a ringdown reference generator for generating a ringdown reference signal, and modifying the reference signal to provide a modified reference signal comprising a weighted sum of the reference signal and the filtered beams;

a subtractor for subtracting the modified reference signal from one of the beams to provide an output signal which is substantially free of ringdown artifacts;

a scan converter for converting the output signal to a display signal; and a display responsive to the display signal for providing a visual image;

wherein the ringdown reference generator provides filtered beams $I_n$ in accordance with the relationship:

$$I_n = \beta S_n + (1-\beta) I_{n-1},$$

where $S_n$ is the current transducer signal, $I_{n-1}$ represents previous filtered beams, and $\beta$ is a first weighting factor; and the ringdown reference generator modifies the ringdown reference signal $R_n$ in accordance with the relationship:

$$R_n = \gamma I_n + (1-\gamma) R_{n-1},$$

where $R_{n-1}$ is a previous reference signal and $\gamma$ is a second weighting factor.

46. An ultrasonic imaging system comprising:

a probe assembly having a plurality of elements for transmitting ultrasonic signals and receiving echo signals in response thereto;

at least one amplifier for amplifying signals from the elements, the signals having a ringdown component arising from continued vibration of the elements after the ultrasonic signals are transmitted and a tissue component corresponding to the echo signals;

an analog-to-digital converter for converting the amplified signals to digital signals;

a beam former for transforming the digital signals from a plurality of elements into beams having both a ringdown component and a tissue component;

a filter for reducing noise in the beams;

a ringdown reference generator for generating a ringdown reference signal, and modifying the reference signal to provide a modified reference signal comprising a weighted sum of the reference signal and the filtered beams;

a subtractor for subtracting the modified reference signal from one of the beams to provide an output signal which is substantially free of ringdown artifacts;

a scan converter for converting the output signal to a display signal; and a display responsive to the display signal for providing a visual image;

wherein the ringdown reference generator provides filtered beams $I_n$ in accordance with the relationship:

$$I_n=\beta S_n+(1-\beta)I_{n-1},$$

where $S_n$ is the current transducer signal, $I_{n-1}$ represents previous filtered beams, and β is a first weighting factor, and the ringdown reference generator modifies the ringdown reference signal $R_n$ in accordance with the relationship:

$$R_n=(I_n+R_{n-1}\cdot W_1)/(1+W1)$$

where $R_{n-1}$ is a previous reference signal and W1 is another weighting factor.

47. An ultrasonic imaging system comprising:

a probe assembly having a plurality of elements for transmitting ultrasonic signals and receiving echo signals in response thereto;

at least one amplifier for amplifying signals from the elements, the signals having a ringdown component arising from continued vibration of the elements after the ultrasonic signals are transmitted and a tissue component corresponding to the echo signals;

an analog-to-digital converter for converting the amplified signals to digital signals;

a beam former for transforming the digital signals from a plurality of elements into beams having both a ringdown component and a tissue component;

a filter for reducing noise in the beams;

a ringdown reference generator for generating a ringdown reference signal, and modifying the reference signal to provide a modified reference signal comprising a weighted sum of the reference signal and the filtered beams;

a subtractor for subtracting the modified reference signal from one of the beams to provide an output signal which is substantially free of ringdown artifacts;

a scan converter for converting the output signal to a display signal; and a display responsive to the display signal for providing a visual image;

wherein the ringdown reference generator provides filtered beams $I_n$ in accordance with the relationship:

$$I_n=\beta S_n+(1-\beta)I_{n-1},$$

where $S_n$ is the current transducer signal, $I_{n-1}$ represents previous filtered beams, and β is a first weighting factor; and the ringdown reference generator modifies the ringdown reference signal $R_n$ in accordance with the relationship:

$$R_n=(I_n+R_{n-1})/2$$

where $R_{n-1}$ is a previous ringdown reference signal.

48. In a method of reducing ringdown artifacts which arise in an ultrasonic imaging system when transducer elements which transmit ultrasonic signals and receive echo signals continue to vibrate after being stimulated to transmit the ultrasonic signals, the steps of:

providing a ringdown reference signal;

modifying the ringdown reference signal to provide a modified reference signal comprising a weighted sum of the ringdown reference signal and filtered transducer signals which contain an echo component and a ringdown component from the transducer elements; and subtracting the modified reference signal from one of the transducer signals to provide an output signal which is substantially free of ringdown artifacts, where $I_n$ represents the filtered transducer signals and is determined in accordance with the relationship:

$$I_n = \left(\sum_{n}^{n+Avg\,Interval} S_n\right)/(Avg\,Interval)$$

where $S_n$ is the current transducer signal, $I_{n-1}$ represents previous filtered transducer signals, and β is a first weighting factor; and the modified reference signal $R_n$ is determined in accordance with the relationship:

$$R_n=\gamma I_n+(1-\gamma)R_{n-1},$$

where $R_{n-1}$ is a previous reference signal and γ is a second weighting factor.

49. A method of generating a modified reference signal, comprising the steps of:

providing a reference signal ($R_{n-1}$); and calculating a modified reference signal $R_n$ in accordance with the relationship:

$$R_n=\gamma I_n+(1-\gamma)R_{n-1},$$

where $I_n$ represents filtered transducer signals and γ is a weighting factor.

* * * * *